(12) United States Patent
Hegland et al.

(10) Patent No.: US 7,761,985 B2
(45) Date of Patent: Jul. 27, 2010

(54) METHOD OF MANUFACTURING A MEDICAL LEAD

(75) Inventors: Michael Hegland, Mounds View, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 817 days.

(21) Appl. No.: 11/343,752

(22) Filed: Jan. 31, 2006

(65) Prior Publication Data

US 2006/0168805 A1    Aug. 3, 2006

Related U.S. Application Data

(60) Provisional application No. 60/648,635, filed on Jan. 31, 2005.

(51) Int. Cl.
*H01R 43/16* (2006.01)
(52) U.S. Cl. .............................. 29/874; 29/825; 29/844; 29/861; 607/115; 607/116; 607/117; 607/118
(58) Field of Classification Search .................. 29/874, 29/825, 844, 854, 861; 607/101, 115–118, 607/122, 132
See application file for complete search history.

(56) References Cited

U.S. PATENT DOCUMENTS

| 452,220 | A | 5/1891 | Gunning |
|---|---|---|---|
| 3,474,791 | A | 10/1969 | Bentov |
| 3,485,247 | A | 12/1969 | Ackerman |
| 3,646,940 | A | 3/1972 | Timm et al. |
| 3,911,928 | A | 10/1975 | Lagergren |
| 3,949,757 | A | 4/1976 | Sabel |
| 3,974,834 | A | 8/1976 | Kane |
| 4,602,645 | A | 7/1986 | Barrington et al. |
| 4,735,205 | A | 4/1988 | Chachques et al. |
| 4,744,370 | A | 5/1988 | Harris |
| 4,961,434 | A | 10/1990 | Stypulkowski |
| 4,969,468 | A | 11/1990 | Byers et al. |
| 5,000,194 | A | 3/1991 | Van Den Honert et al. |
| 5,114,744 | A | 5/1992 | Cloutier et al. |
| 5,127,403 | A | 7/1992 | Brownlee |

(Continued)

FOREIGN PATENT DOCUMENTS

EP    1201198    5/2002

(Continued)

OTHER PUBLICATIONS

Xu, Shi-Ang, et al., Comparison of Half-Band and Full-Band Electrodes for Introcochlear Electrical Stimulation, Ann. Otol. Rhinol. Laryngol., 1993, pp. 363-367, vol. 102.

*Primary Examiner*—Thiem Phan
(74) *Attorney, Agent, or Firm*—Stephen Bauer; Rick L. Franzen

(57) ABSTRACT

A method of manufacturing a segmented electrode assembly. An electrically conducting tube is coupled to an electrically insulating material. The tube is generally cylindrical and hollow and defines one or more gaps at a first axial position. The tube also includes one or more bridges located at a second axial position. The method includes removing at least a portion of the bridge resulting in a segmented electrode assembly having at least one segment. A number embodiments of making a tube are also provided. In another embodiment a method of manufacturing a medical lead using a segmented electrode assembly is provided.

32 Claims, 43 Drawing Sheets

U.S. PATENT DOCUMENTS

| | | | |
|---|---|---|---|
| 5,147,590 A | 9/1992 | Preidel et al. |
| 5,374,285 A | 12/1994 | Vainani et al. |
| 5,405,373 A | 4/1995 | Petersson et al. |
| 5,423,877 A | 6/1995 | Mackey |
| 5,455,998 A | 10/1995 | Miyazono et al. |
| 5,489,275 A | 2/1996 | Thompson et al. |
| 5,501,703 A | 3/1996 | Holsheimer et al. |
| 5,522,874 A | 6/1996 | Gates |
| 5,562,722 A | 10/1996 | Racz et al. |
| 5,578,067 A | 11/1996 | Ekwall et al. |
| 5,582,609 A | 12/1996 | Swanson et al. |
| 5,643,339 A | 7/1997 | Kavteladze et al. |
| 5,649,970 A | 7/1997 | Loeb et al. |
| 5,713,944 A | 2/1998 | Kroll |
| 5,728,149 A | 3/1998 | Laske et al. |
| 5,800,465 A | 9/1998 | Thompson et al. |
| 5,824,030 A | 10/1998 | Yang et al. |
| 5,843,148 A | 12/1998 | Gijsbers et al. |
| 5,895,416 A | 4/1999 | Barreras, Sr. et al. |
| 5,913,882 A | 6/1999 | King |
| 5,919,222 A | 7/1999 | Hjelle et al. |
| 5,927,277 A | 7/1999 | Baudino et al. |
| 5,938,690 A | 8/1999 | Law et al. |
| 6,011,996 A | 1/2000 | Gielen et al. |
| 6,038,480 A | 3/2000 | Hrdlicka et al. |
| 6,052,624 A | 4/2000 | Mann |
| 6,113,572 A * | 9/2000 | Gailey et al. ............. 604/93.01 |
| 6,134,478 A | 10/2000 | Spehr |
| 6,178,354 B1 | 1/2001 | Gibson |
| 6,212,434 B1 | 4/2001 | Schreiner et al. |
| 6,236,892 B1 | 5/2001 | Feler |
| 6,240,320 B1 | 5/2001 | Spehr et al. |
| 6,253,109 B1 | 6/2001 | Gielen |
| 6,319,241 B1 | 11/2001 | King et al. |
| 6,393,325 B1 | 5/2002 | Mann et al. |
| 6,466,811 B1 | 10/2002 | Hassett |
| 6,473,653 B1 | 10/2002 | Schallhorn et al. |
| 6,493,590 B1 | 12/2002 | Wessman et al. |
| 6,498,049 B1 | 12/2002 | Friend et al. |
| 6,510,347 B2 | 1/2003 | Borkan |
| 6,526,321 B1 | 2/2003 | Spehr |
| 6,587,733 B1 | 7/2003 | Cross, Jr. et al. |
| 6,666,864 B2 | 12/2003 | Bencini et al. |
| 6,721,604 B1 | 4/2004 | Robinson et al. |
| 6,895,280 B2 | 5/2005 | Meadows |
| 6,895,283 B2 | 5/2005 | Erickson |
| 7,142,903 B2 * | 11/2006 | Rodriguez et al. .......... 600/374 |
| 2001/0053885 A1 | 12/2001 | Gielen et al. |
| 2002/0022872 A1 | 2/2002 | Gielen et al. |
| 2002/0027336 A1 | 3/2002 | Ross et al. |
| 2002/0183817 A1 | 12/2002 | Van Venrooij |
| 2003/0083724 A1 | 5/2003 | Jog et al. |
| 2004/0098074 A1 | 5/2004 | Erickson et al. |
| 2005/0015130 A1 | 1/2005 | Gill |

FOREIGN PATENT DOCUMENTS

| | | |
|---|---|---|
| GB | 1147532 | 4/1969 |
| WO | WO 87/01947 | 4/1987 |

* cited by examiner

ATTACHING ONE OR MORE RODS TO AN INNER SURFACE OF AN OUTER COMPONENT — 502

FIG. 6

METHOD OF MANUFACTURING A MEDICAL LEAD

RELATED APPLICATION

This application claims priority to provisional U.S. Application Ser. No. 60/648,635, filed Jan. 31, 2005 which is incorporated by reference.

TECHNICAL FIELD

The invention relates to medical devices and methods, more particularly to a method of manufacturing an implantable medical lead having a segmented electrode for electrically stimulating the human body or for sensing.

BACKGROUND

The medical device industry produces a wide variety of electronic and mechanical devices for treating patient medical conditions such as pacemakers, defibrillators, neurostimulators and therapeutic substance delivery pumps. Medical devices may be configured to be surgically implanted or connected externally to the patient receiving treatment. Clinicians use medical devices alone or in combination with therapeutic substance therapies and surgery to treat patient medical conditions. For some medical conditions, implantable medical devices provide the best and sometimes the only therapy to restore an individual to a more healthy condition and a fuller life.

An implantable neurological stimulation system may be used to treat conditions such as pain, movement disorders, epilepsy, depression, pelvic floor disorders, gastroparesis, and a wide variety of other medical conditions. Such a neurostimulation system typically includes an implantable neurostimulator, a medical electrical stimulation lead, and an extension such as that shown in the Medtronic, Inc. brochure "Implantable Neurostimulation System" (1998). More specifically, the neurostimulator system may be an Itrel II® Model 7424 or an Itrel 3® Model 7425 available from Medtronic, Inc. of Minneapolis, Minn. that may be used to treat conditions such as pain, movement disorders and pelvic floor disorders. The neurostimulator is typically connected to a stimulation lead that has one or more electrodes to deliver electrical stimulation to a specific location in the patient's body.

Some therapies involve electrical stimulation of the brain and others involve stimulation of the spinal cord. Still other therapies involve electrical stimulation of other sites in the patient's body.

Among the various types of implantable medical electrical leads employed to treat pain by electrically stimulating a patient's spinal cord or portions thereof are the Medtronic PISCES QUAD Model No. 3487A and PISCES Z QUAD Model No. 3890, 3891 and 3892 medical electrical leads. These leads are designed to be percutaneously introduced near a patient's spinal cord, and aid in the management of chronic, intractable pain via pulsed electrical stimulation through nerve structures in the dorsal aspect of the spinal cord. Activation of the stimulated structures produces nerve impulses that often inhibit the transmission of pain.

Currently commercially available PISCES leads have four platinum iridium electrodes mounted on the distal ends of the leads. Each electrode is 3 mm long and is spaced 6 mm from the adjacent electrode(s). Each PISCES electrode has a ring shape and extends around the circumference of the lead body. At the proximal end of a PISCES lead is an in-line four-conductor connector for mechanical and electrical attachment to a lead extension or an implantable stimulator. Each electrode thus has a single unique electrical conductor associated with it.

Experience with the PISCES series of leads has shown that intraoperative stimulation tests and lead position adjustments should generally be performed on a patient to ascertain optimal lead position and orientation. Various electrode configurations, locations and orientations are tested to obtain appropriate parasthesia during surgery, repositioning the lead as necessary. Certain precautions may be taken during surgery to minimize the risk that lead position will shift post-operatively, such as anchoring the distal portion of the lead with non-biodegradable sutures to the supra-spinous ligament or deep fascia. Despite careful testing, positioning and anchoring of percutaneously spinal cord stimulation leads during surgery, however, in some patients inadequate or minimal therapeutic effect is nevertheless obtained. In still other patients, leads may shift position post-operatively, resulting in inadequate or no parasthesiatic effect.

Segmented electrodes (also referred to as segments herein), which are electrodes that do not extend around the full circumference of the lead body at the point of stimulation (e.g., may extend anywhere from about 1 degree of arc to about 359 degrees of arc), may be desired for targeted stimulation or for efficient use of energy. For example, for deep brain stimulation it may be desirable to stimulate on only one side of the lead while avoiding stimulation on the other side (in which case a single segment of about 180 degrees may be one solution). Or it may be desirable to stimulate on one side of the lead under certain conditions and the other side under different conditions or at a different time (one solution for this may be to have two or more segments each of 60, 100, 120 or 160 degrees of arc (for example) at the same axial position or location on the lead).

One concern with segmented medical leads is the interaction between the electrode and the lead body. Ring shaped electrodes used for non-segmented electrodes do not generally share this problem because the ring shape holds the electrode to the lead body. Lead failure by a segmented electrode pulling away from the lead body is cause for concern. Such a failure not only possibly results in an inoperative lead, but also presents the significant problem of how to remove the lead from the patient's body without harming surrounding tissue. A lead is desired that solves this problem and is easily manufactured.

The foregoing and other features and advantages, which will now become more readily apparent by referring to the following specification, drawings and claims, are provided by the various embodiments of the present invention.

SUMMARY

In a first embodiment, a method of manufacturing a segmented electrode assembly is provided. An electrically conducting tube is coupled to an electrically insulating material. The tube is generally cylindrical and hollow and defines one or more gaps at a first axial position. The tube also includes one or more bridges located at a second axial position. The method includes removing at least a portion of the bridge resulting in a segmented electrode assembly having at least one segment. A number embodiments of making a tube are also provided.

In another embodiment, a method of manufacturing a medical lead is provided. A segmented electrode assembly is made. The segmented electrode assembly is placed on a conductor assembly having at least one conductor. The conductor is electrically coupled to a segment of the assembly. This combined conductor assembly and segmented electrode assembly are placed in a mold and an electrically insulating material is injected into the mold to create a medical lead.

BRIEF DESCRIPTION OF THE DRAWINGS

FIG. 6 shows a flowchart of another embodiment of making a tube which may then be used in the making of a segmented electrode assembly;

DETAILED DESCRIPTION

Figure 1:
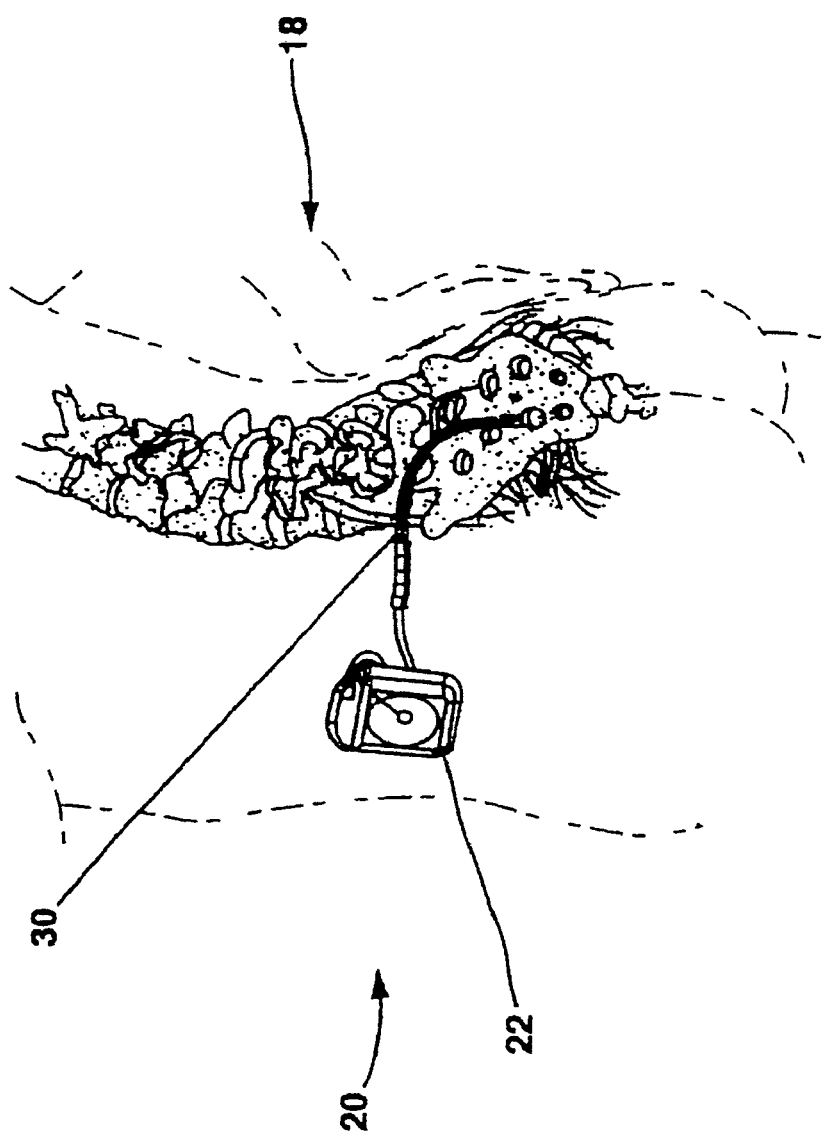
FIG. 1 shows a general view of one embodiment of a neurostimulation system.
Figure 2:
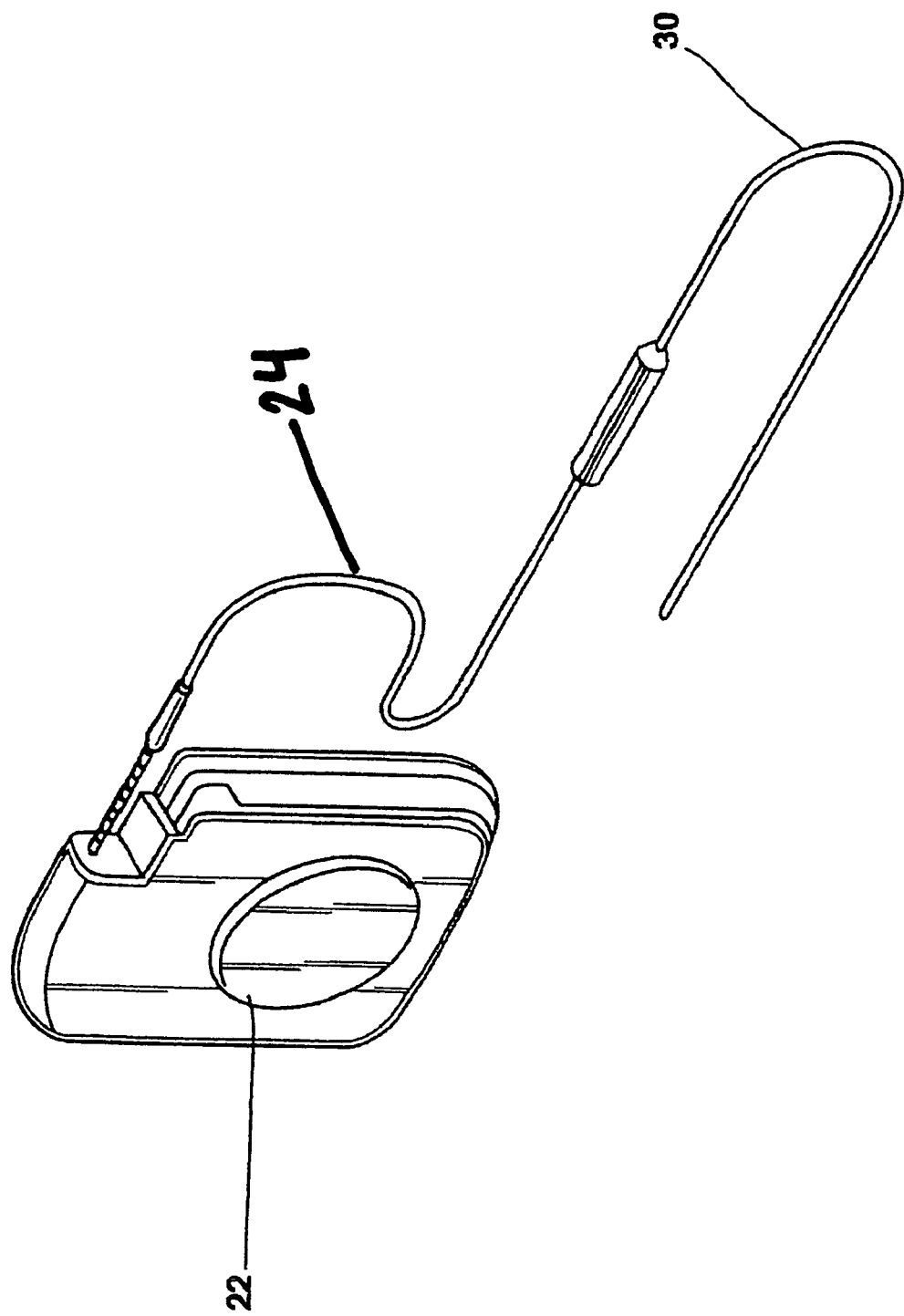
FIG. 2 shows some components of one embodiment of a neurostimulation system.

FIG. 1 shows a general view of one embodiment of a neurostimulation system implanted within a patient. It should be understood however that the invention is not limited to the manufacture of leads for neurostimulation. The manufacturing techniques provided herein may be used for manufacturing leads for use in stimulating anywhere in the body. FIG. 2 shows some components of one embodiment of neurostimulation system. Neurostimulation systems are used to treat conditions such as pain, movement disorders, epilepsy, pelvic floor disorders, gastroparesis, and a wide variety of other medical conditions. The neurostimulation system 20 includes a neurostimulator 22 such as a Restore® neurostimulator available from Medtronic, Inc. in Minneapolis, Minn., a stimulation lead extension 24, and a stimulation lead 30. The neurostimulator 22 is typically implanted subcutaneously in the patient's body 18 at a location selected by the clinician. The stimulation lead 30 is typically fixed in place near the location selected by the clinician using a device such as the adjustable anchor. Implantable lead 30 may be configured as a neurological stimulation lead, a neurological sensing lead, and a combination of both as a neurological stimulation and sensing lead, a cardiac lead, and the like.

FIGS. 3-7 are flowcharts illustrating various methods of manufacturing segmented electrode assemblies and incorporating those segmented electrode assemblies into medical leads. FIGS. 8-11 illustrate various stages of the manufacture of segmented electrode assemblies according to a first embodiment. FIGS. 12-17 illustrate various stages of a method of manufacturing a lead using segmented electrode assemblies according to the first embodiment. FIGS. 18-28 illustrate various stages of the manufacture of segmented electrode assemblies according to a second embodiment. FIGS. 29-35 illustrate various stages of the manufacture of segmented electrode assemblies according to a third embodiment. FIGS. 36-43 illustrate various stages of the manufacture of segmented electrode assemblies according to a fourth embodiment.

Figure 3:
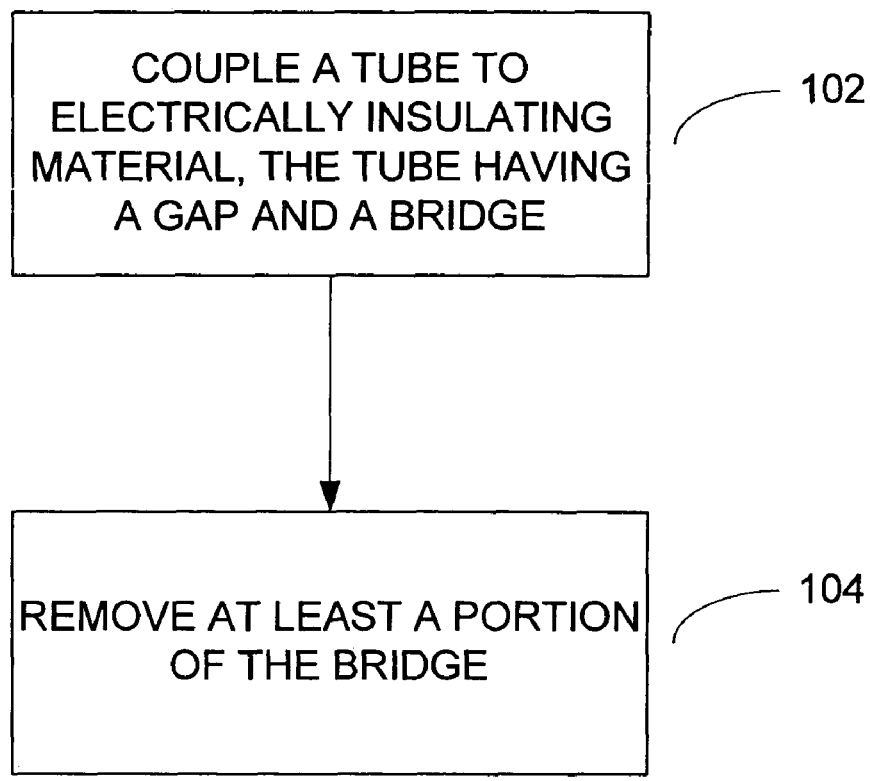
FIG. 3 shows a flowchart of a method of making a segmented electrode assembly.

FIG. 3 is a flowchart illustrating a method of manufacturing a medical lead assembly according to one embodiment of the invention. The medical lead assembly so manufactured may then be incorporated into the construction of a medical lead as is discussed further below. At block 102, a tube is coupled to an electrically insulating material. A tube is any generally cylindrically shaped member that includes at least on its outer surface an electrically conducting material. Examples of tubes are shown in FIGS. 9, 18, 29 and 36 as tubes 700, 800, 900 and 1000. A tube may be a one piece member or it may be constructed from more than one piece. For example, tube 700 is a one piece member. Tubes 800, 900 and 1000 are constructed by attaching multiple components together as is described in detail below. A tube includes a portion that will eventually become one or more electrode segments. An electrode segment (also referred to as a segment) is an electrode that does not extend around the entire circumference of the lead. The tube also includes at least one gap and at least one bridge. A gap in a tube is any opening, aperture or slot in the electrically conducting portion of the tube such that the gap provides electrical isolation between adjacent electrode segments once any bridges in the tube are at least partially removed. A bridge is a portion of the tube that either connects adjacent electrode segments or completes the circumference of the tube in the case of only a single electrode segment. The tubes may be hollow. This means that there is some open space in the middle of the tubes for eventual receipt of a conductor assembly.

At block 104, at least a portion of the bridge is removed resulting in a segmented electrode assembly having at least one segment. As will be discussed in more detail below, the coupled electrically insulating material holds the electrode segment or segments to the assembly so that the bridge(s) are no longer needed. Removal of the bridge or bridges or at least a portion thereof allows the segment(s) to be electrically isolated from each other. One embodiment of removing a bridge or portion of a bridge is to cut through the coupled tube and electrically insulating material at a location that removes the electrical connection between adjacent segments. Cutting for purposes herein includes grinding.

Figure 4:
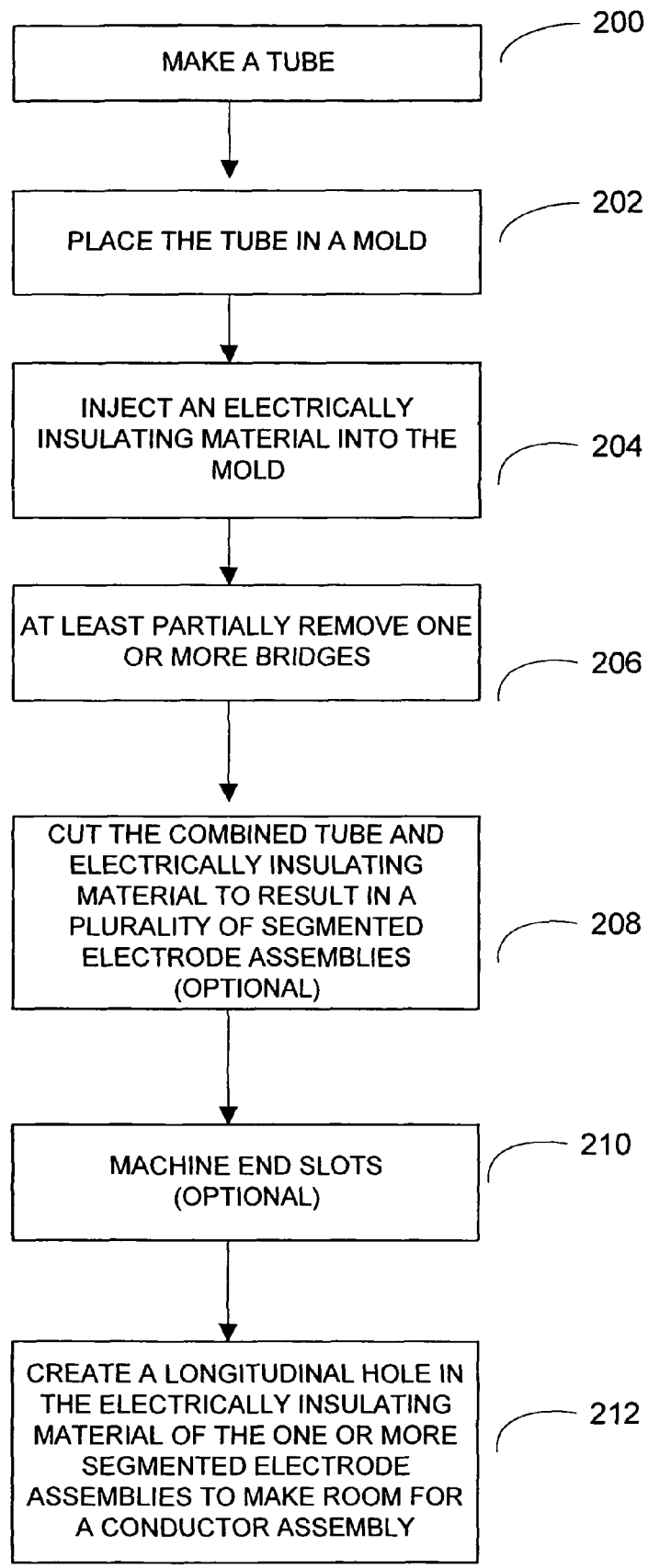
FIG. 4 shows a flowchart of one embodiment method of making a segmented electrode assembly.
Figure 8:
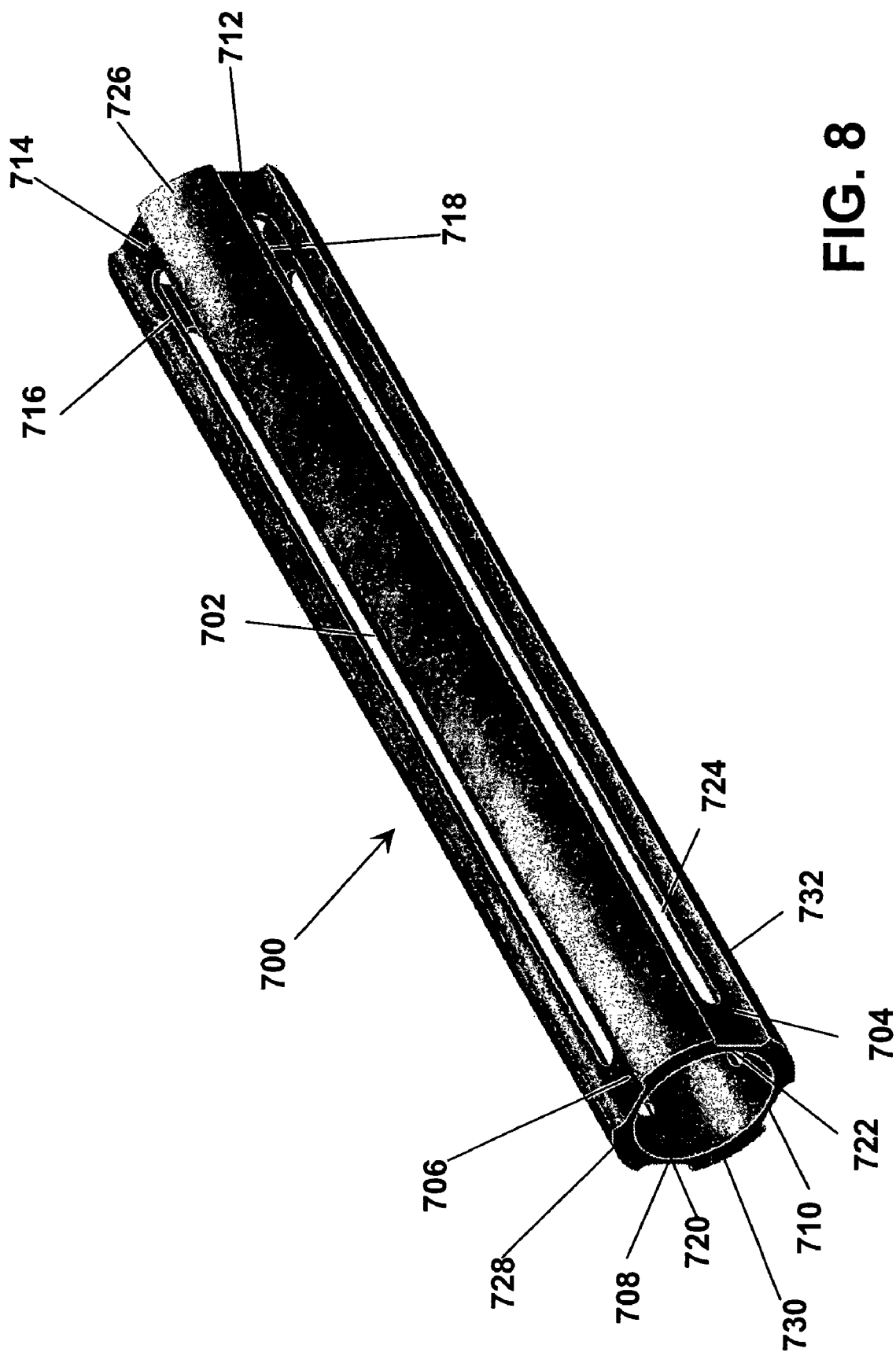
FIG. 8 is a perspective view of a first embodiment tube
Figure 9:
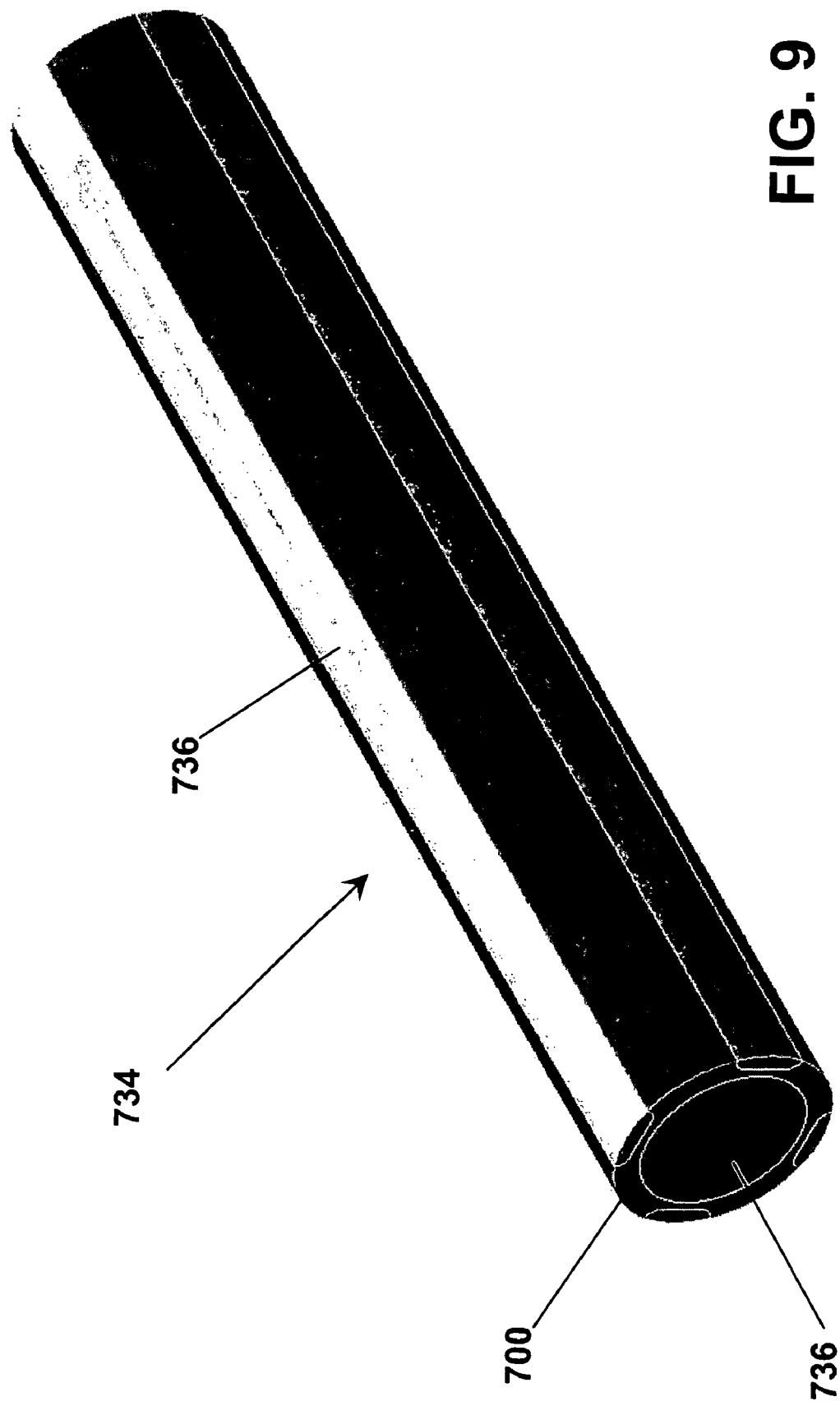
FIG. 9 is a perspective view of a first embodiment coupled tube and electrically insulating material before removal of electrically insulating material for the conductor assembly and before creation of end slots.
Figure 10:
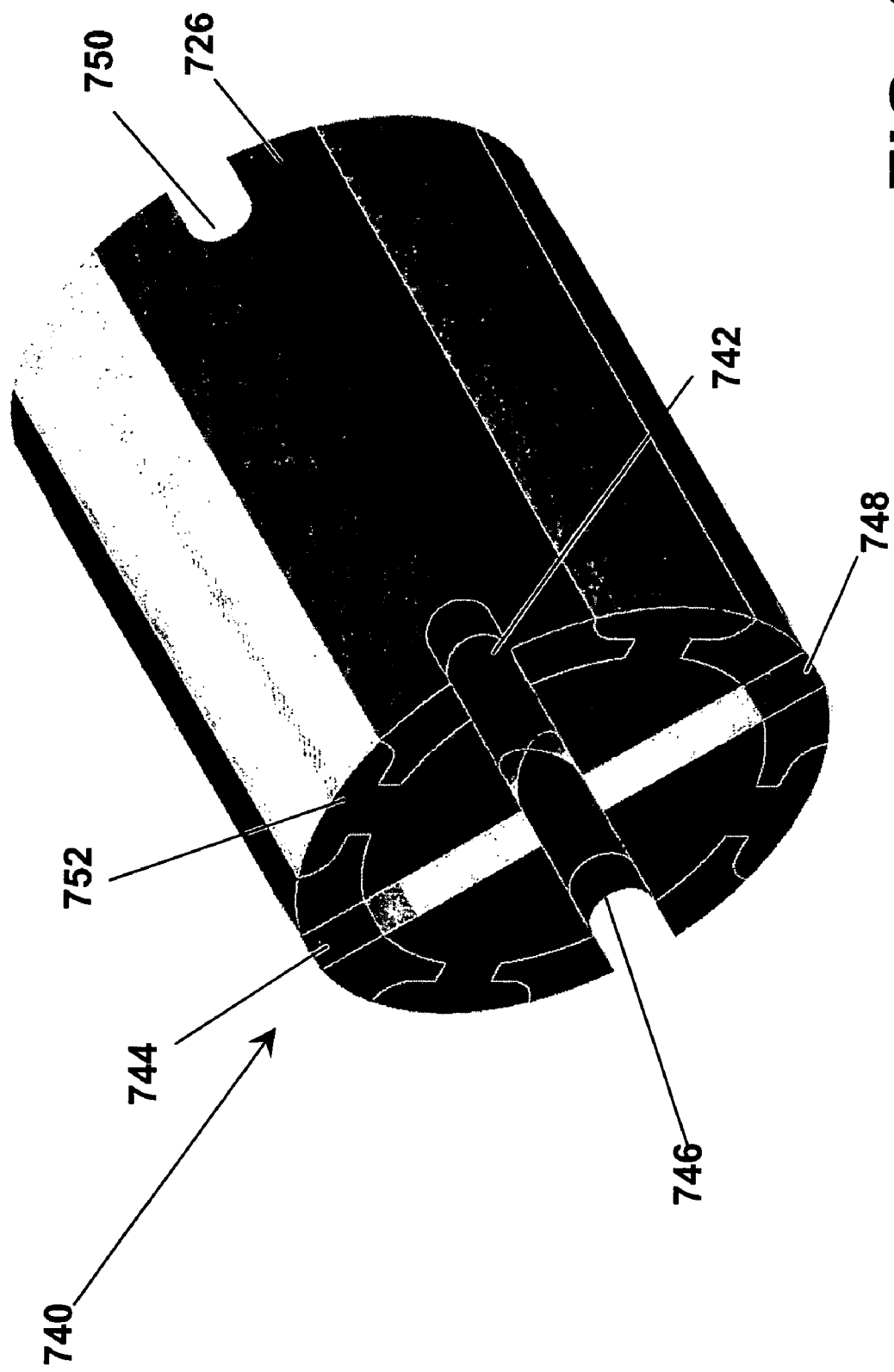
FIG. 10 is a perspective view of a partially completed segmented electrode assembly with end slots.
Figure 11:
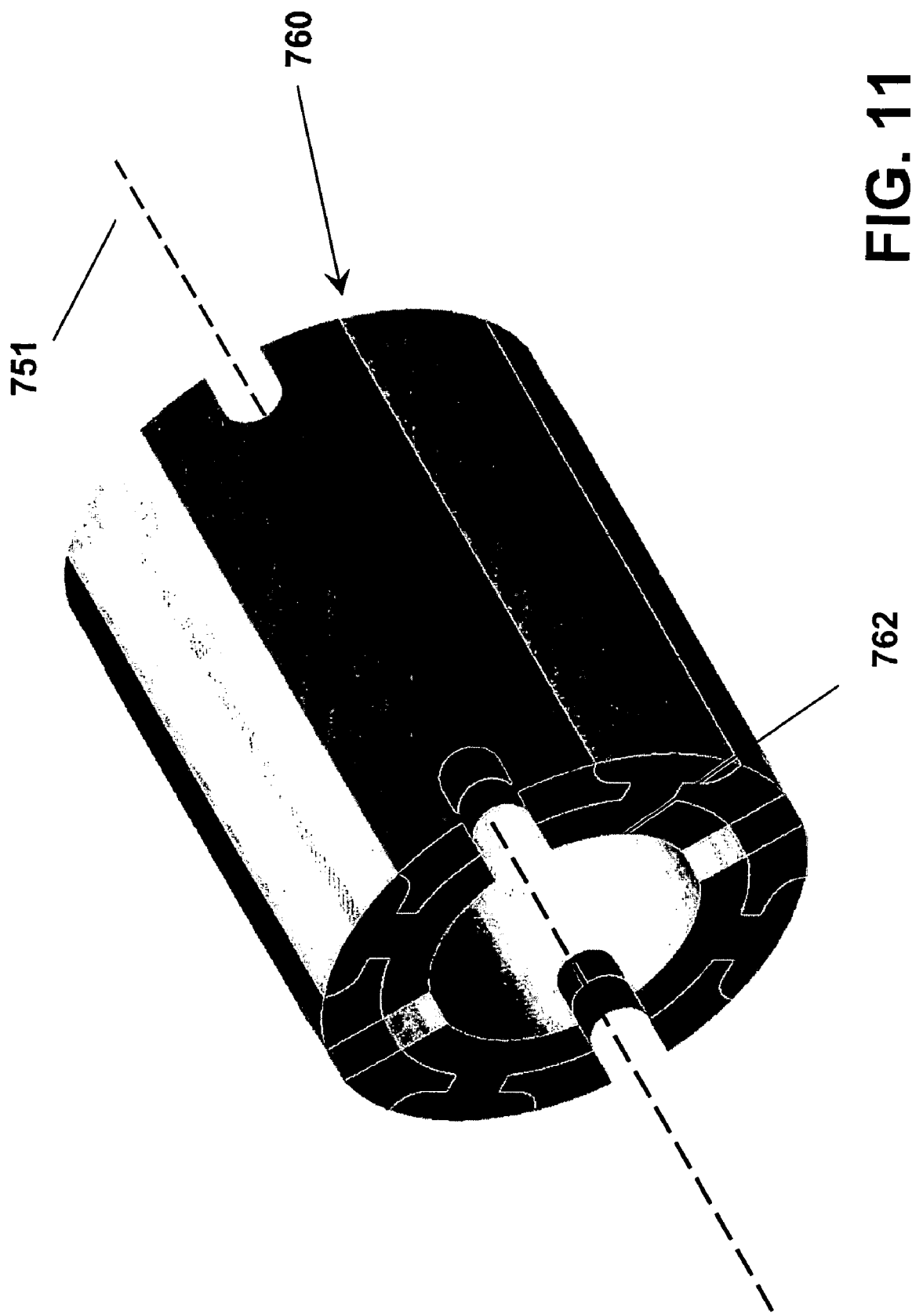
FIG. 11 is a perspective view of a segmented electrode assembly with drilled hole for receipt of a conductor assembly.

FIG. 4 is a flowchart providing a more detailed embodiment of a method of manufacturing a segmented electrode assembly. FIGS. 9-11 show various stages of such manufacturing according to one embodiment. Block 200 represents making the tube. There are many embodiments of making a tube as are described further below. In one embodiment tube 700 of FIG. 8 is made by starting with cylindrical tubing and milling it in the longitudinal direction for each gap and two corresponding bridges desired. This particular example tube 700 has 4 gaps (702, 720, 722, and 724) corresponding with the fact that the segmented electrode assembly being made in this example will have 4 segments (726, 728, 730, and 732). So to make tube 700, the tubing is milled in four different circumferential locations corresponding with the four gaps desired and the area around the gaps having a smaller wall thickness than the locations of the segments. In one embodiment tube, start with 0.050" 90%-10% Pt/Ir tubing that has 0.006" wall thickness and mill using a 0.005" end mill. This particular tube 700 also includes 8 bridges (704, 706, 708, 710, 712, 714, 716 and 718) corresponding to two bridges per gap (one on each end of the tube). In the case of a single segment assembly, the tube may have only a single gap and one or more bridges. The bridge in this case would complete the circumference of the tube. The gaps 702, 720, 722 and 724 in the tube are created by laser-cutting.

The tube is then placed in a mold at block 202 and insert molded by injecting an electrically insulating material into the mold at block 204. One embodiment of the resulting coupled tube and insulating material member is shown in FIG. 9 as member 734 that includes tube 700 and electrically insulating material 736. In one embodiment, electrically insulating material 736 is PEEK (polyetheretherketone) or polysulfone. At block 206, one or more or all bridges are removed or partially removed to electrically isolate the segments from each other. In one embodiment, the bridges are removed by cutting off the ends of the tube after it has been coupled with the electrically insulating material. At block 208, additional cuts may be made in the member 734 if multiple segmented electrode assemblies are being manufactured out of a single member 734. At block 210, end slots are machined into one or more of the segments. Machining may be performed by many different methods including, but not limited to, drilling, laser machining, EDM (electrical discharge machining), plasma cutting. These end slots are for accommodating receipt and connection of the conductors to the segments. FIG. 10 illustrates an almost completed segmented electrode assembly 740 having eight end slots (only five shown) 742, 744, 746, 748 and 750. Note that the milled area of the tube 700 results in a retaining surface (e.g., surface 752) which results in the electrically insulating material holding the segments (e.g., segment 726) in place along their full length and preventing them from pulling or peeling away from the assembly after the bridge(s) are removed. Also note that machining end slots on both ends of a segmented electrode assembly allows the assemblies to be placed on a conductor assembly either end first. In order to accommodate a conductor assembly running down the center of the segmented electrode assembly, a hole is created in the electrically insulating material along the longitudinal axis of the member 734 at block 212. In one embodiment, the hole is created by drilling. For purposes of this application, drilling includes boring. FIG. 11 shows the completed segmented electrode assembly 760 after such drilling to create the hole 762. In the embodiment shown in FIG. 11, the diameter of the hole 762 is such that a layer of insulating material remains on the inside surfaces of the segments. In an alternative embodiment, the hole 762 in the segmented electrode assembly 760 may be obtained by inserting a pin into the tube before coupling the tube with the electrically insulating material. In this way the hole 762 is reserved as the injected insulating material is not allowed to be injected into that space. After injection is completed, the pin may be removed and the end slots machined.

Figure 12:
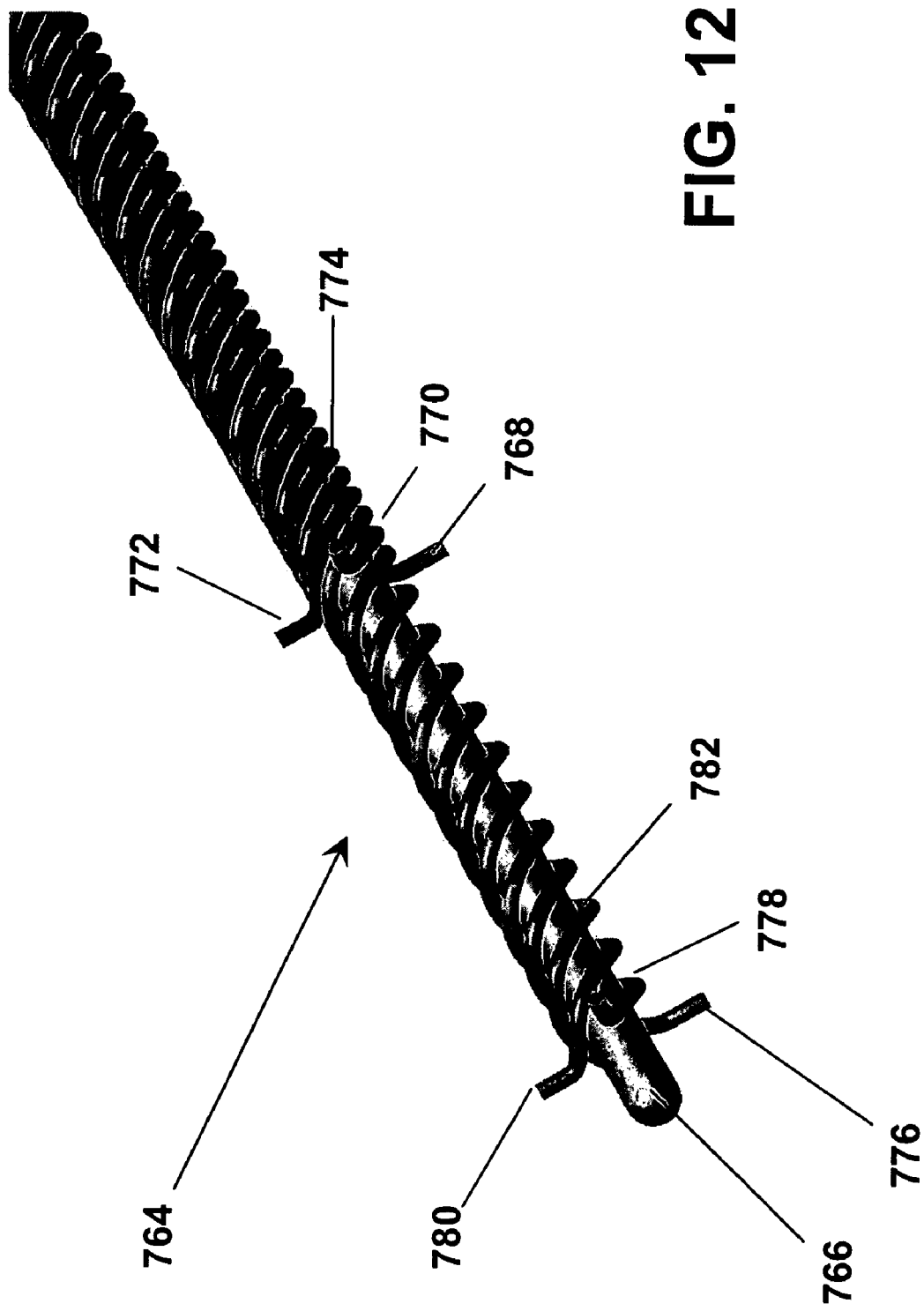
FIG. 12 is a perspective view of one embodiment conductor assembly.
Figure 15:
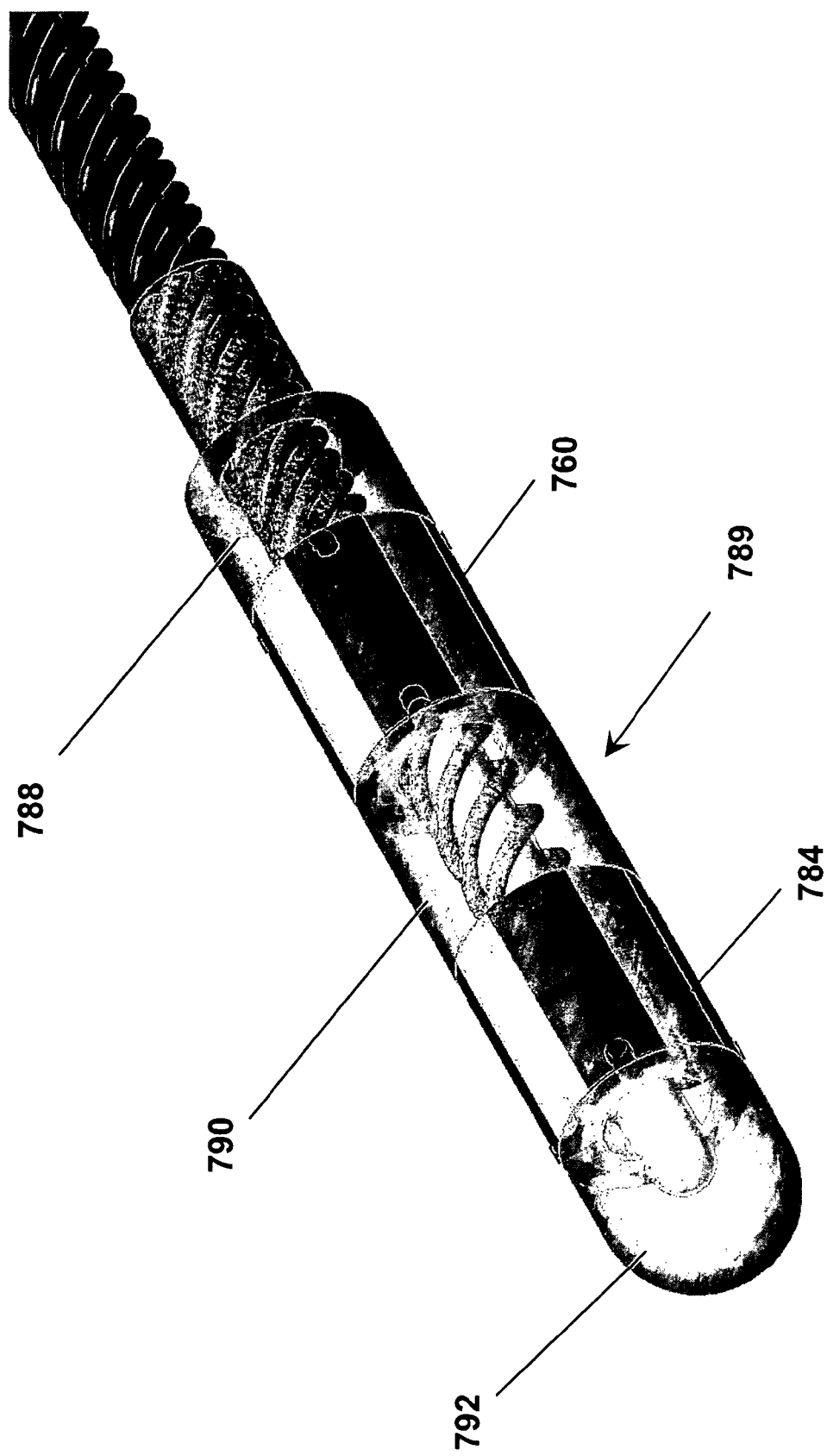
FIG. 15 is a perspective view of the distal end of the medical lead of FIG. 14 after being overmolded with an electrically insulating material.
Figure 16:
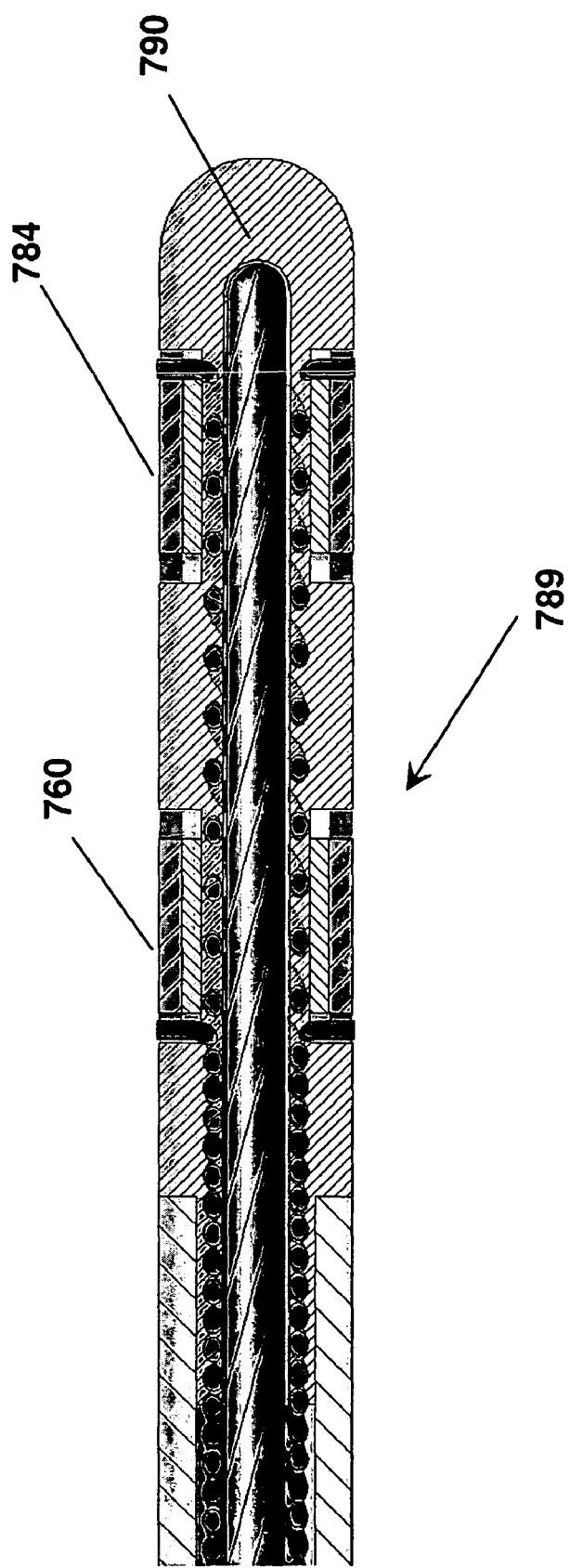
FIG. 16 is a cross sectional view of the medical lead of FIG. 15.
Figure 17:
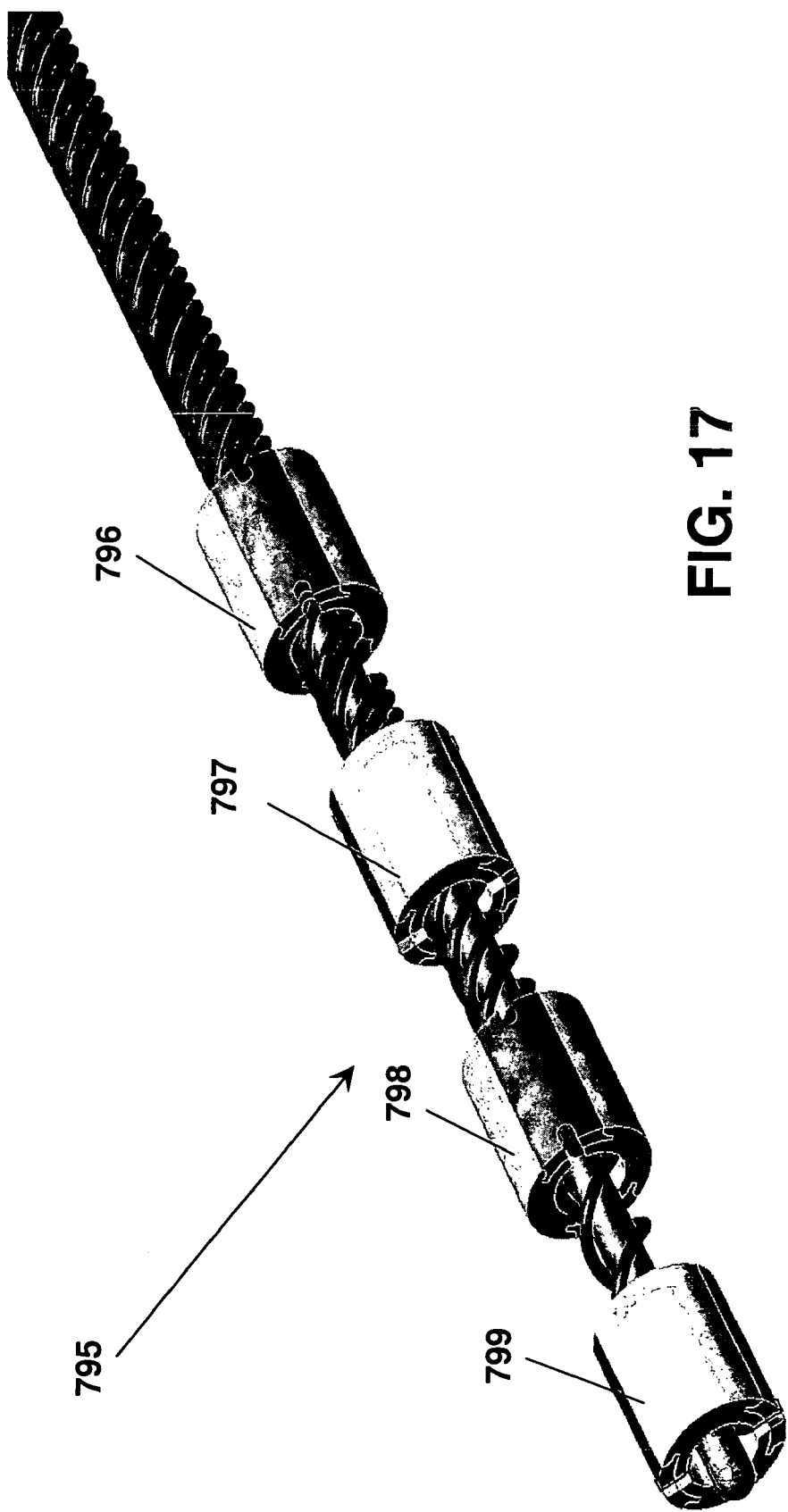
FIG. 17 is a perspective view of an alternative embodiment medical lead manufactured according to the method of this invention and having four segmented electrode assemblies on a conductor assembly before being overmolded with an electrically insulating material.
Figure 18:
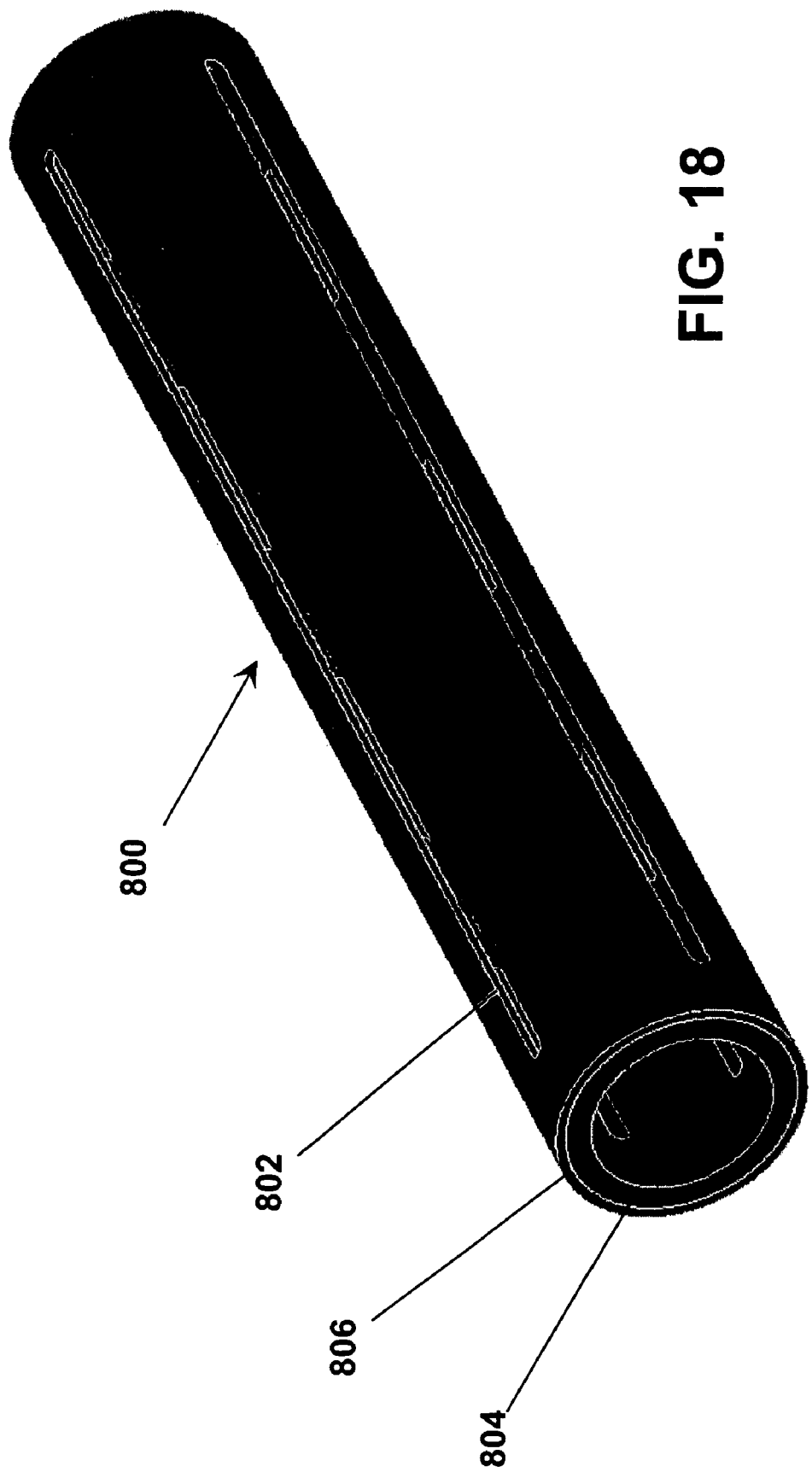
FIG. 18 is a perspective view of a second embodiment tube.

Once a segmented electrode assembly is made, one or more segmented electrode assemblies may be used to make a medical lead. This process is now described in conjunction with FIG. 7. At block 602 one or more segmented electrode assemblies are made. At block 604 the one or more segmented electrode assemblies are placed on a conductor assembly along the longitudinal axis of the segmented electrode assembly or assemblies. FIG. 12 illustrates one embodiment of a conductor assembly. A conductor assembly is one or more conductors and supporting structure if any. The conductors may be in any configuration such as straight line or coiled. The number of conductors in the conductor assembly depends on the number of electrodes and whether or not electrodes are to be electrically coupled together. For example, if the lead is to have two segmented electrode assemblies each with four segments, then eight conductors are used. One such embodiment is shown in FIGS. 12-16. Another embodiment lead 795 may have four segmented electrode assemblies 796, 797, 798 and 799 each with two segments as shown in FIG. 17. This embodiment also has eight conductors. Another embodiment may have four segmented electrode assemblies each having four segments. In such an embodiment, sixteen conductors may be used.

The conductors may be manufactured from a wide range of materials that are electrically conductive such as MP35N, platinum and the like. In some embodiments, a conductor may comprise a plurality of wires that may be configured as braided strand wire (BSW). BSW is available in many configurations including seven wire BSW. When low impedance is desired, the core of each wire may be manufactured from a low impedance metal such as silver and the jacket may be manufactured from a material with good mechanical strength properties such as MP35N. One embodiment of conductor uses seven wire BSW with a silver core and an MP35N jacket typically with a resistance of less than about 0.098 ohms/cm (3 ohms/foot) and a tensile strength greater than SN. The conductor may be electrically insulated with a flouro-polymer such as ethyletetraflouroethylene with a coating thickness of approximately 0.0002 cm (0.0008 inch).

Figure 13:
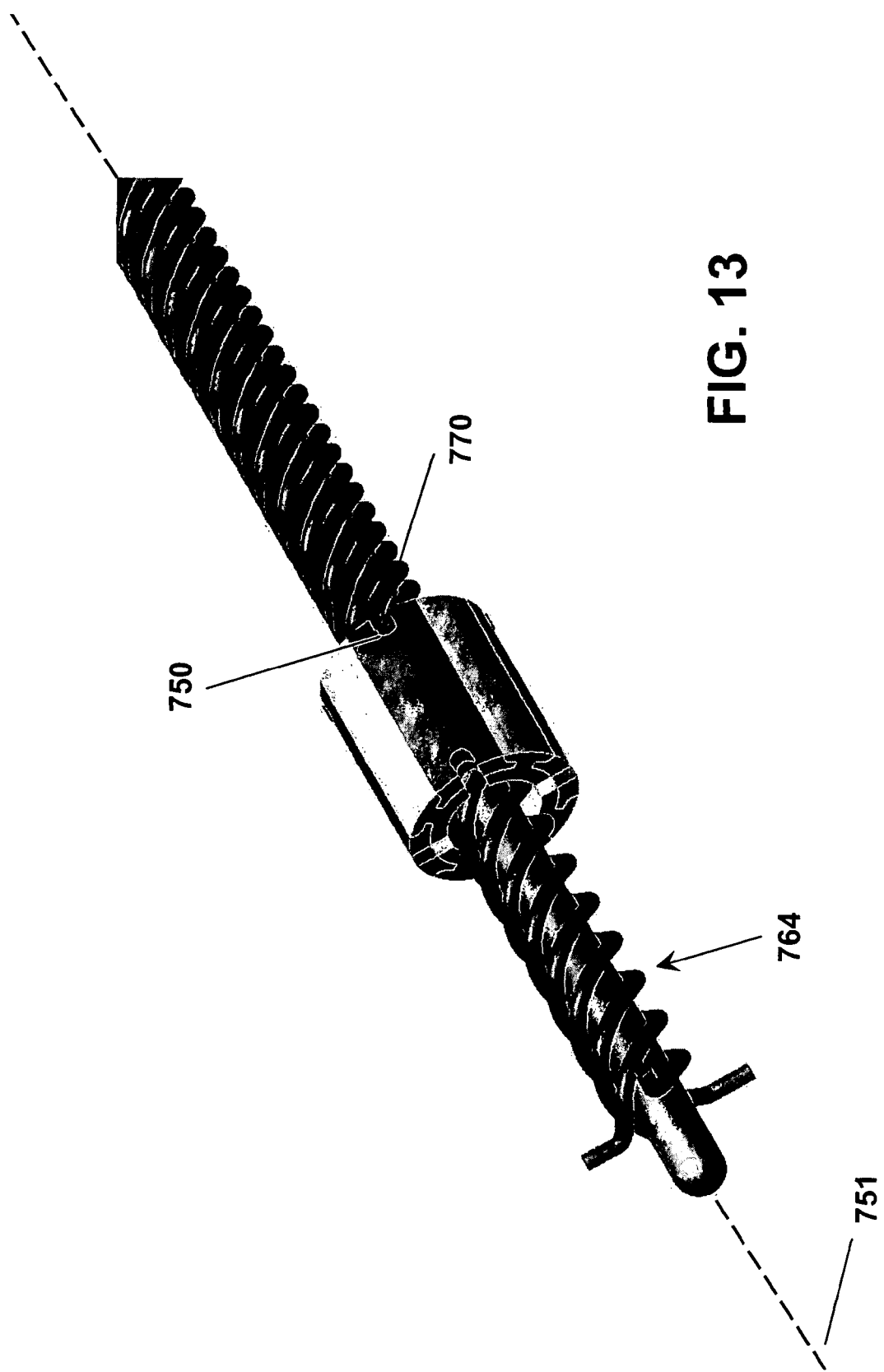
FIG. 13 is a perspective view of a segmented electrode assembly placed on the conductor assembly of FIG. 12.
Figure 14:
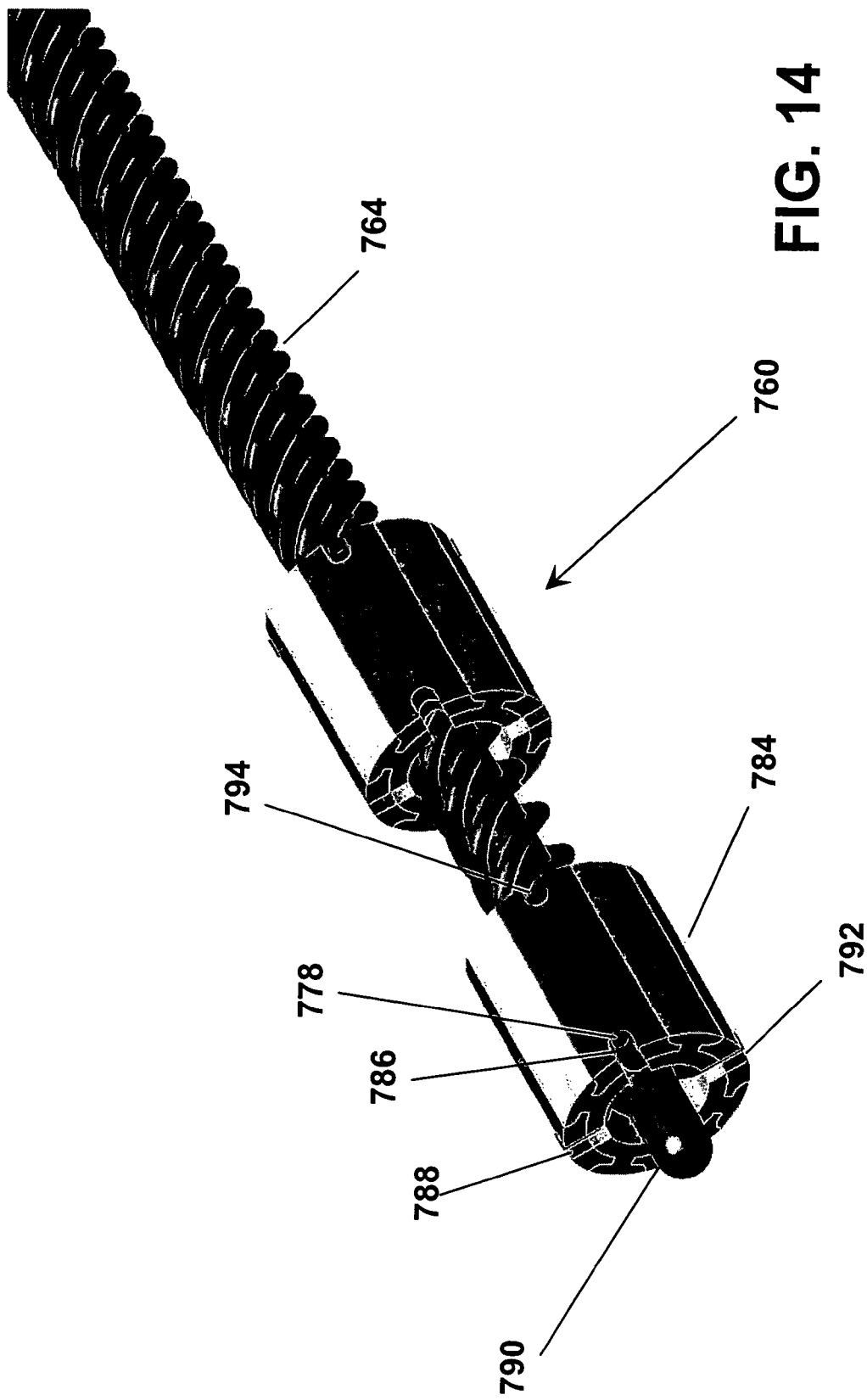
FIG. 14 is a perspective view of a two segmented electrode assemblies placed on the conductor assembly of FIG. 12.

Conductor assembly 764 includes 8 conductors (768, 770, 772, 774, 776, 778, 780, 782) coiled around a stylet receiving member 766. Four of the conductors (768, 770, 772,774) terminate at one more proximal axial position and another four conductors (776, 778, 780, 782) terminate at a more distal axial location. In FIG. 13 a first segmented electrode assembly has been placed on the conductor assembly by sliding the first segmented electrode assembly onto the conductor assembly. The conductor assembly is positioned along the longitudinal axis 751 of the first segmented electrode assembly. At block 606 of FIG. 7, the at least one of the one or more conductors of the conductor assembly are electrically coupled to at least one of the one or more segments of the one or more segmented electrode assemblies. One embodiment of this step is shown in FIGS. 13 and 14. The ends of conductors 768, 770, 772, and 774 (shown in FIG. 12) are placed into the four proximal end slots (only proximal end slot 750 is shown in FIG. 13, with the end of conductor 770 shown positioned in the end slot 750). In FIG. 14, a second segmented electrode assembly 784 is placed on the conductor assembly 764. Ends of conductors 776, 778, 780 and 782 are placed into four of the end slots in second segmented electrode assembly 784. Note that either the distal end slots 786, 788, 790 and 792 or the proximal end slots such as end slot 794 or a combination of both distal and proximal end slots may be used for receipt of the ends of conductors 776, 778, 780 and 782. The ends of conductors are electrically coupled to the segments of the segmented electrode assemblies. In one embodiment the conductors are welded to the end slots of the segments for such electrical coupling.

Figure 7:
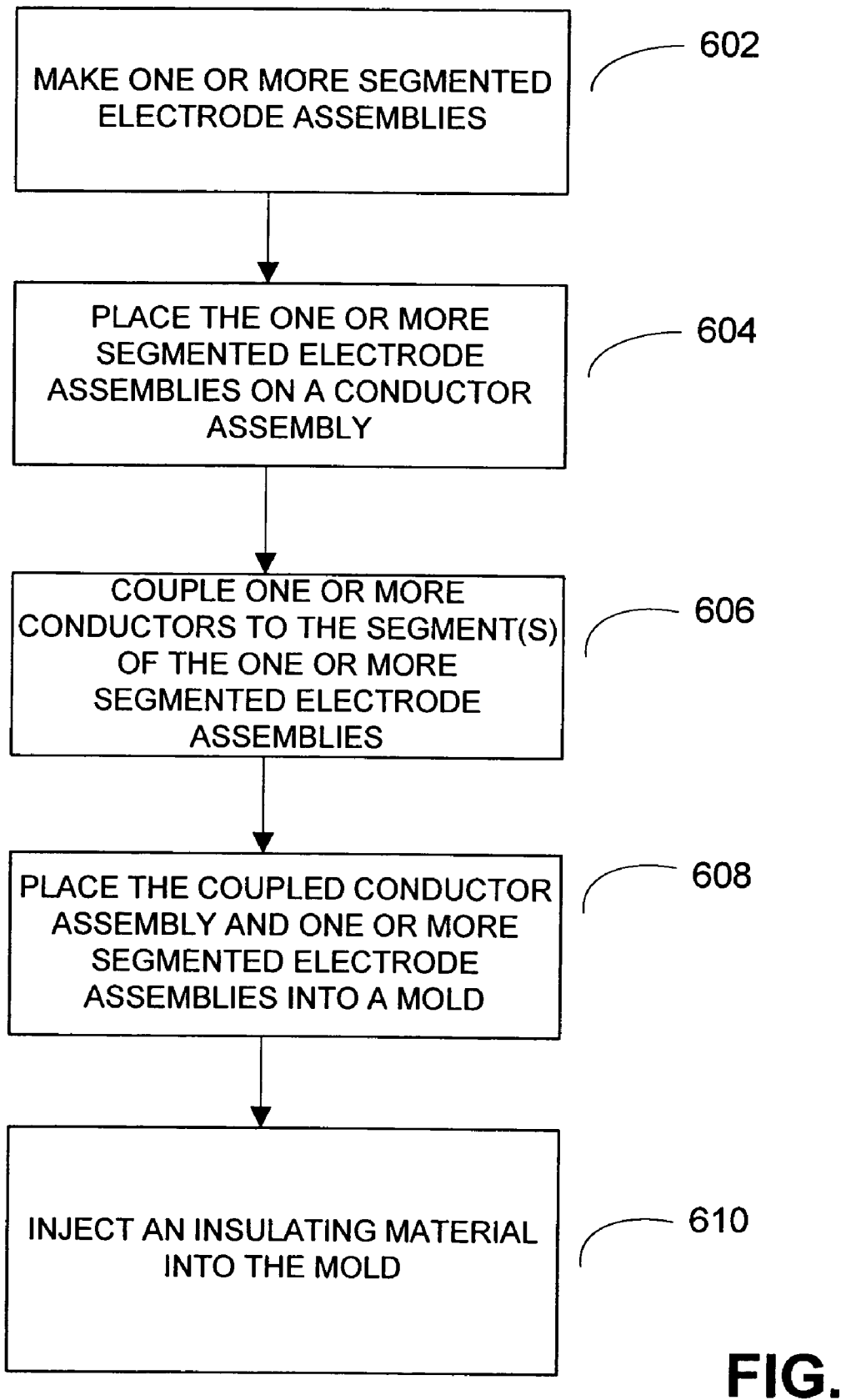
FIG. 7 shows a flowchart of a method of manufacturing a medical lead using one or more segmented electrode assemblies.

At block 608 of FIG. 7, the coupled conductor assembly and one or more segmented electrode assemblies are placed in a mold. In the case of two or more segmented electrode assemblies on a single lead, adjacent segmented electrode assemblies are longitudinally spaced apart or separated by a space. This space is filled or partially filled with a second insulating material. In one embodiment, a second electrically insulating material is injected into the mold at block 610 to provide the spacers 788, 790 between segmented electrode assemblies and may also include the tip 792 of the lead. In one embodiment, the second electrically insulating material is injected slowly at low pressure (e.g., less than 1000 psi) to prevent displacement of electrical conductors and prevent mechanical loading of electrical connections during the injection process. FIG. 15 shows the medical lead 789 after the steps of blocks 608 and 610. In the embodiment shown in FIG. 15, the outer shape of the lead is substantially cylindrical. The second electrically insulating material may be the same or different from the electrically insulating material used in the making of the segmented electrode assemblies. In one embodiment, the second electrically insulating material is polyurethane. This overmolding structurally connects the conductor assembly and the segmented electrode assemblies together as well as provides a smooth outer surface for the distal end of the lead by filling in the spaces between segmented electrode assemblies and the lead tip. Note that the proximal portion of the lead beginning just proximal of spacer 788 may later be covered with a polyurethane tubing that may be bonded to the overmolded spacer 788. FIG. 16 is a cross sectional view of lead 789.

Figure 5:
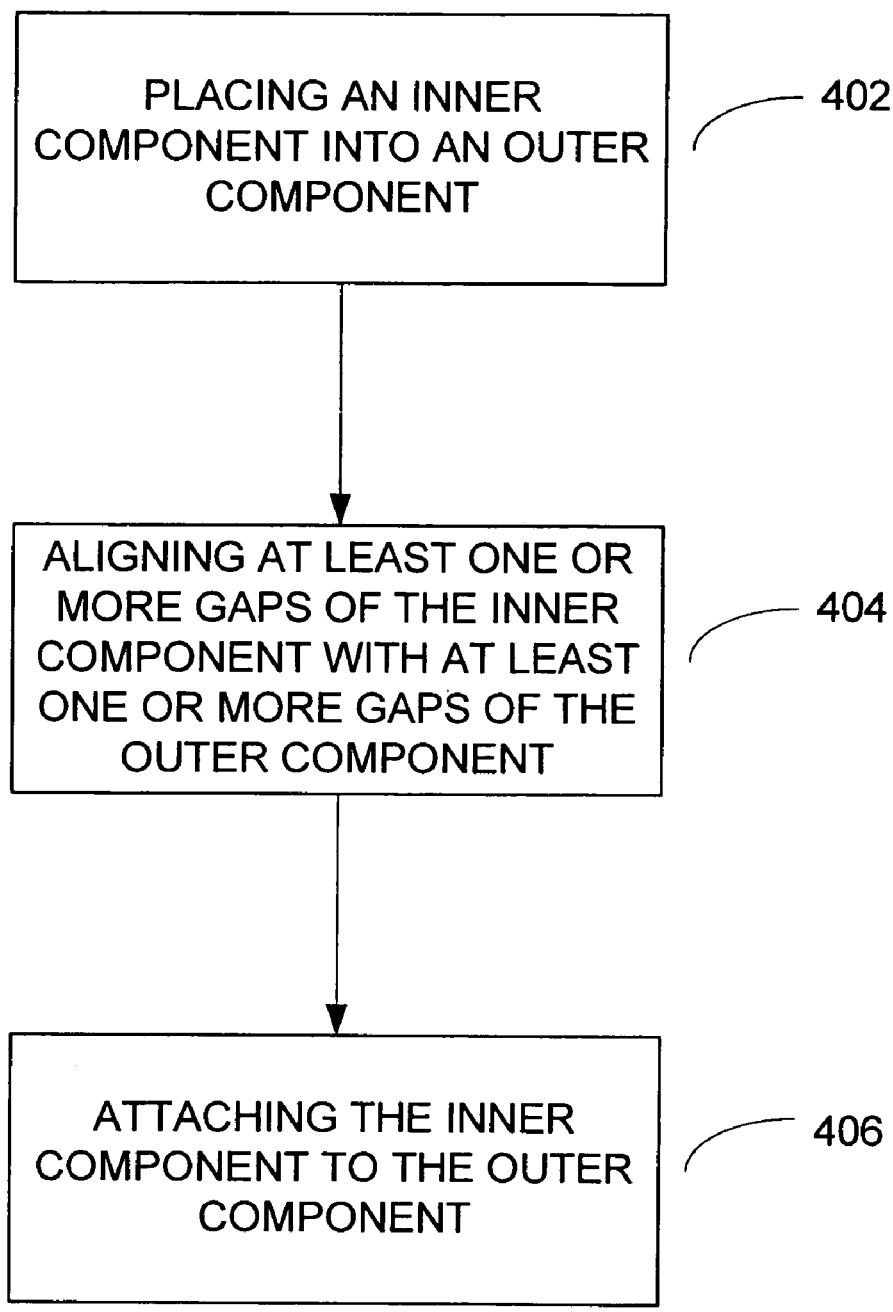
FIG. 5 shows a flowchart of one embodiment of making a tube which may then be used in the making of a segmented electrode assembly.

Returning now to a discussion of making a segmented electrode assembly, there are a number of alternative embodiments of tubes that may be made and/or used. The discussion above referred mostly to the first embodiment shown in FIGS. 8-17. FIG. 5 is a flowchart showing the steps of making a tube according to the second and fourth embodiments of tubes. The second embodiment tube is shown in FIGS. 18-28. The fourth embodiment tube is shown in FIGS. 36-43. Block 402 of FIG. 5 is placing an inner component of the tube into an outer component of the tube. An outer component is generally cylindrical and hollow and defines one or more gaps and one or more bridges. One embodiment of an outer component is shown as outer component 806 in FIG. 19. Outer component 806 includes four gaps such as gap 808. Outer component 806 also includes eight bridges (e.g., bridge 816). An outer component also has an inner surface which is the surface facing inward (toward the hollow space) and an outer surface facing outward. Outer component 806 has inner surface 812 and outer surface 814. The inner component is generally cylindrical and may be hollow. The inner component will also have at least one gap at a first axial position and at least one bridge at a second axial location. One embodiment inner component is inner component 804 in FIG. 19. Inner component 804 includes four gaps including gap 810. Inner component 804 also includes eight bridges (e.g., bridge 818). An inner component also includes an outer surface that faces outward (ultimately facing the inner surface of the outer component. Inner component 804 has an outer surface 820. An inner component may also include an inner surface that faces inward (if the inner component is hollow). Inner component 804 includes inner surface 822.

Figure 19:
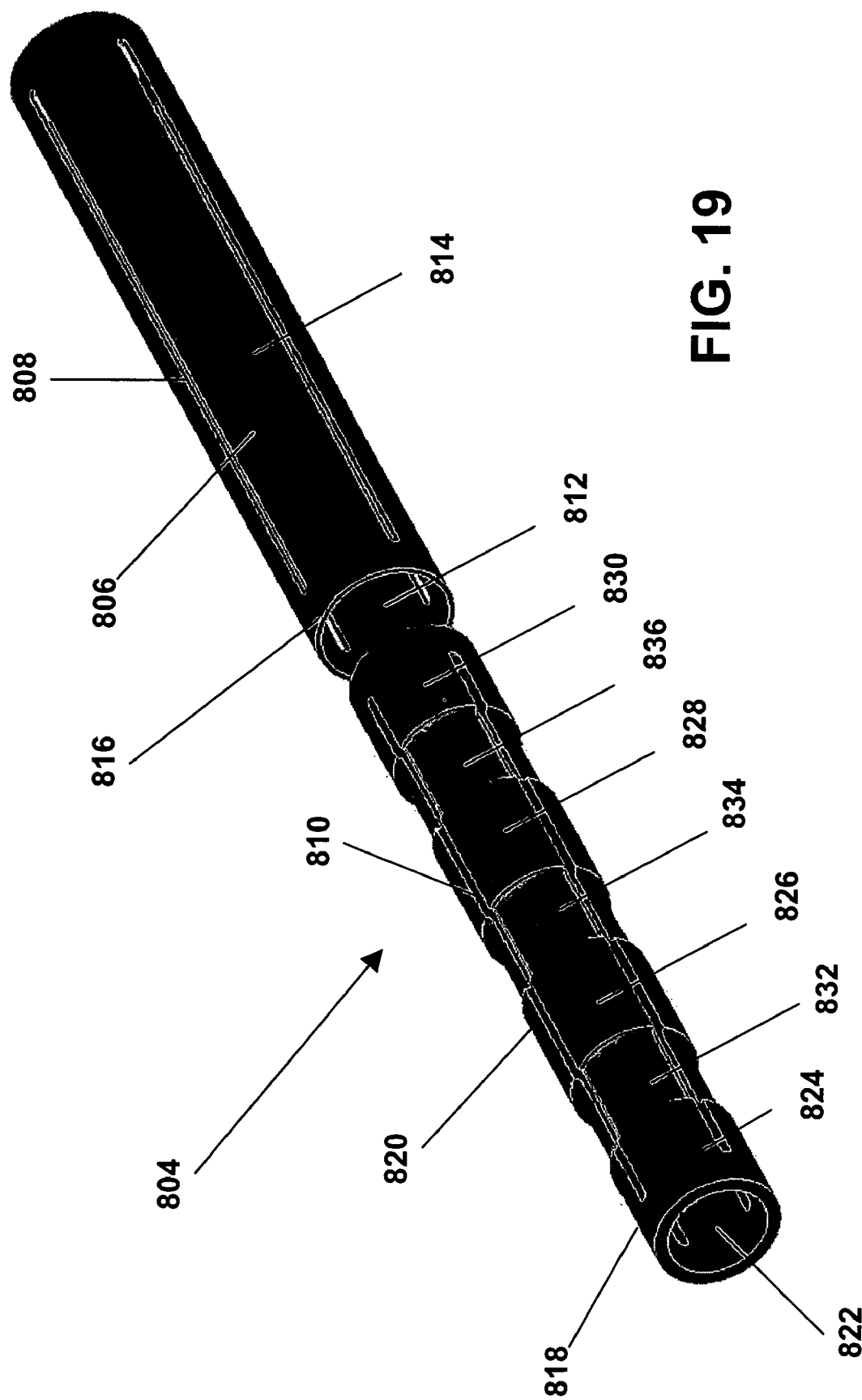
FIG. 19 is an exploded perspective view of the second embodiment tube.
Figure 20:
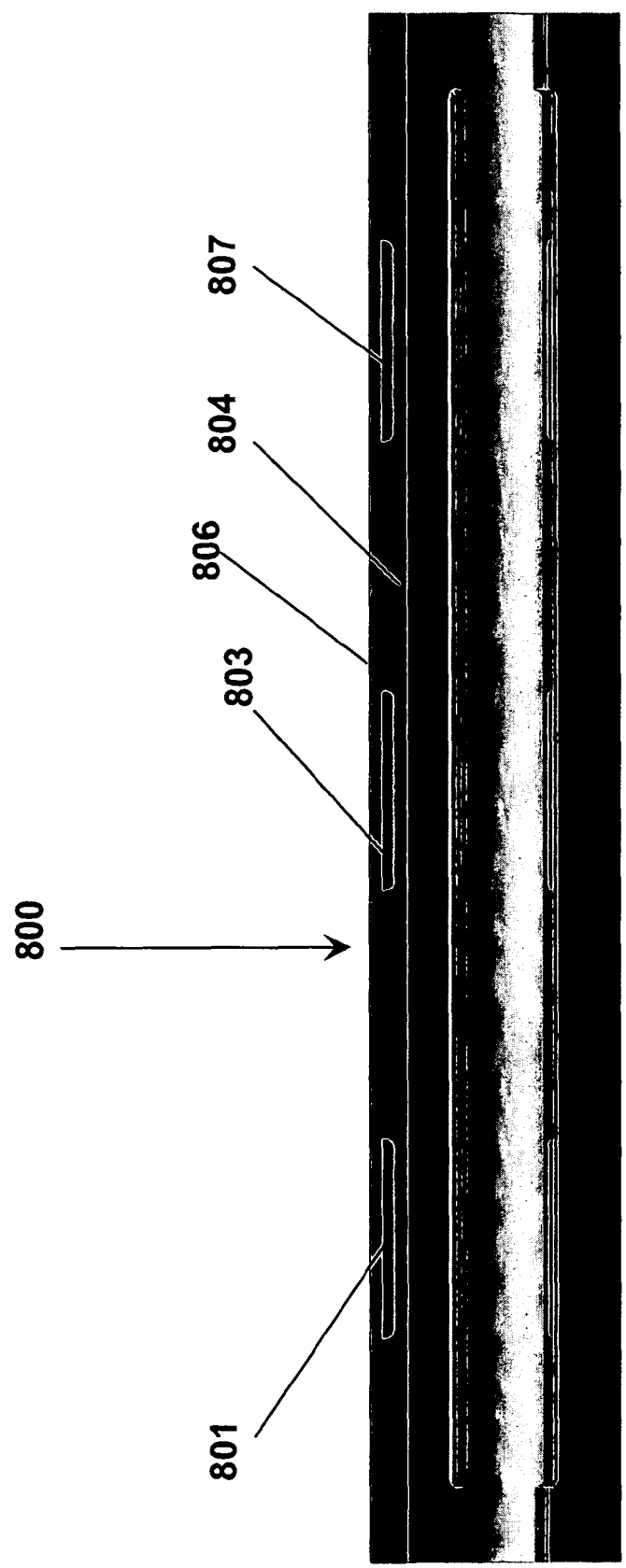
FIG. 20 is a cross sectional view of the tube of FIGS. 18 and 19.
Figure 21:
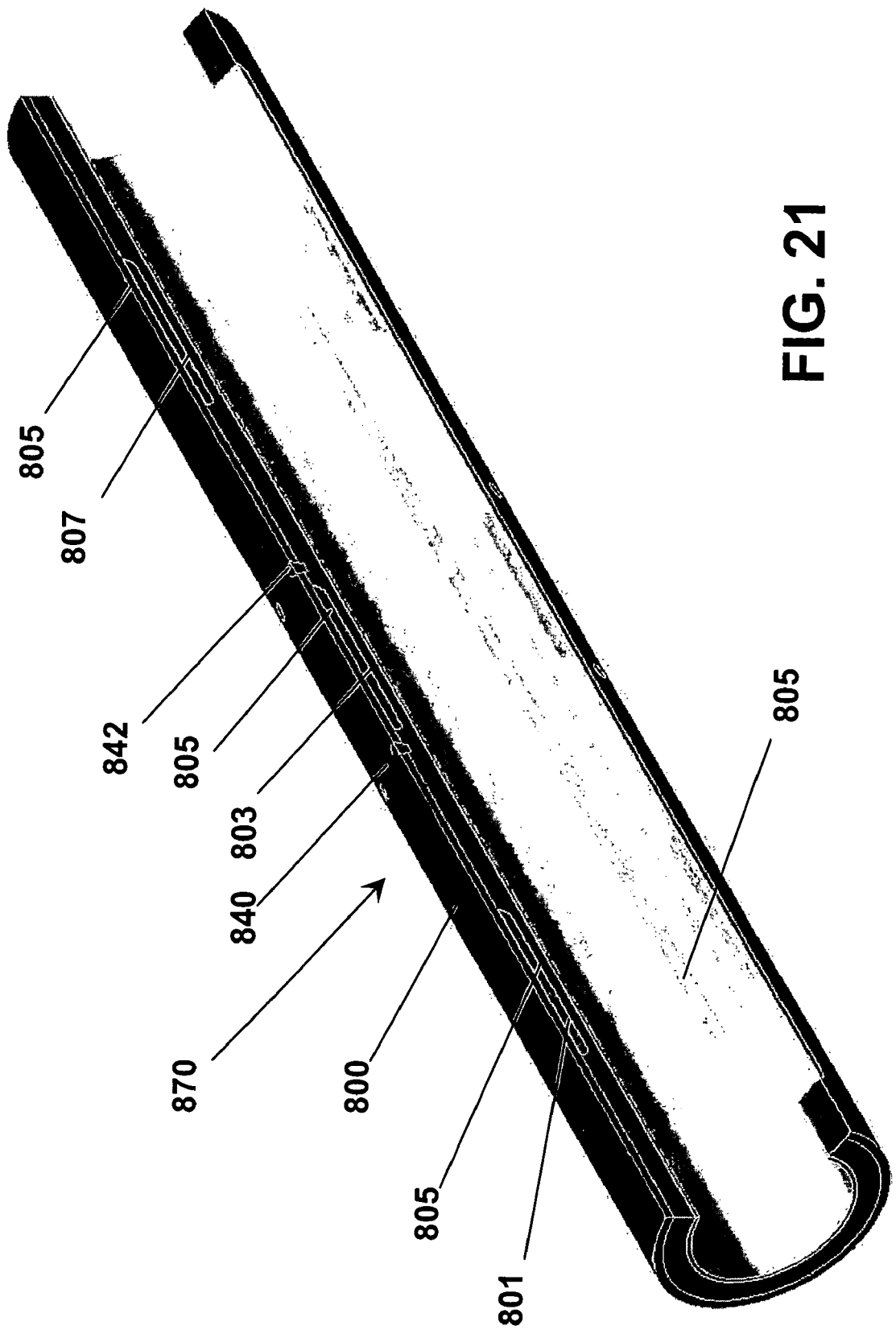
FIG. 21 is a perspective partial cut away view of the second embodiment tube of FIGS. 18 and 19 after being coupled to electrically insulating material.
Figure 22:
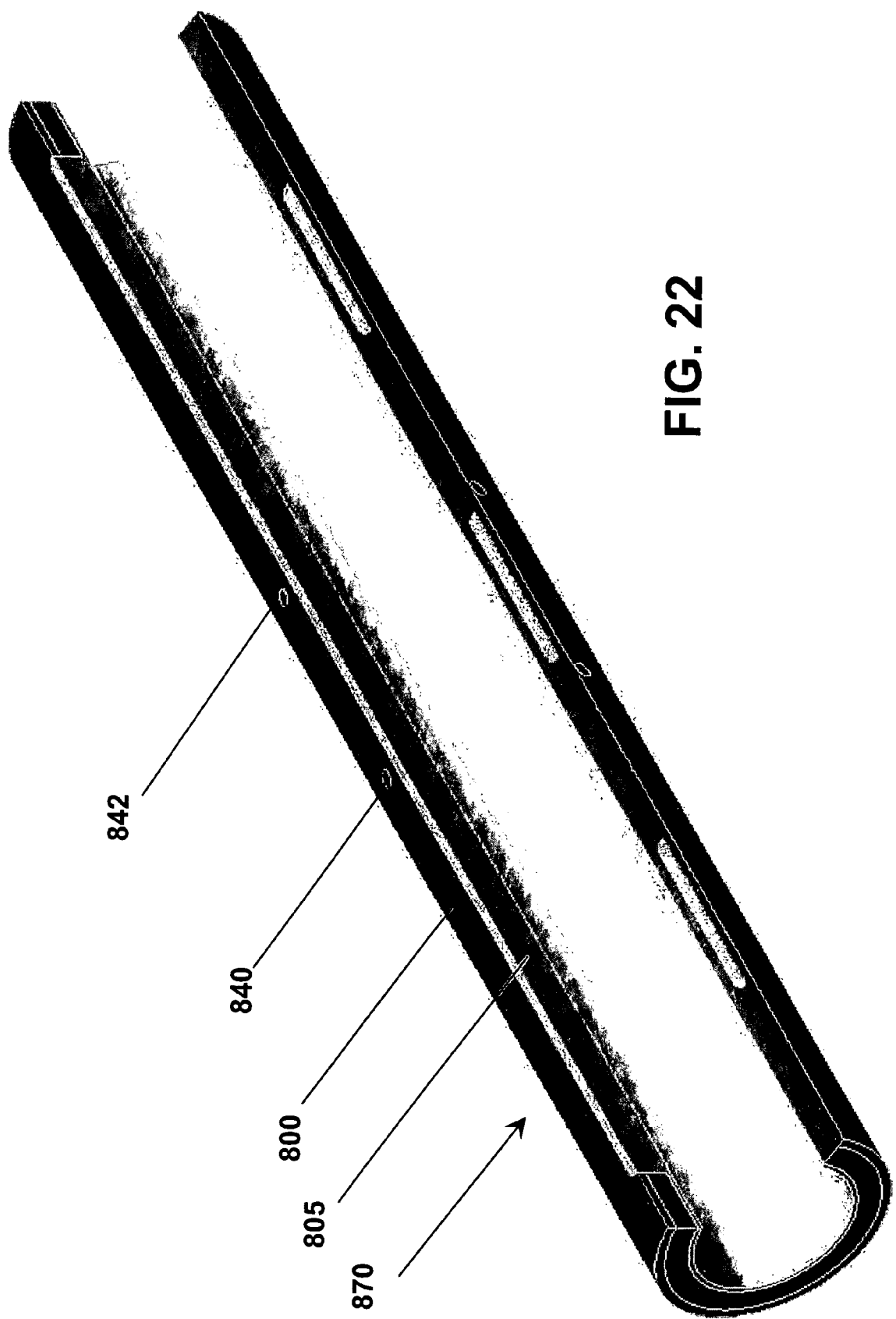
FIG. 22 is a different cut away view of the second embodiment tube and insulating material.
Figure 23:
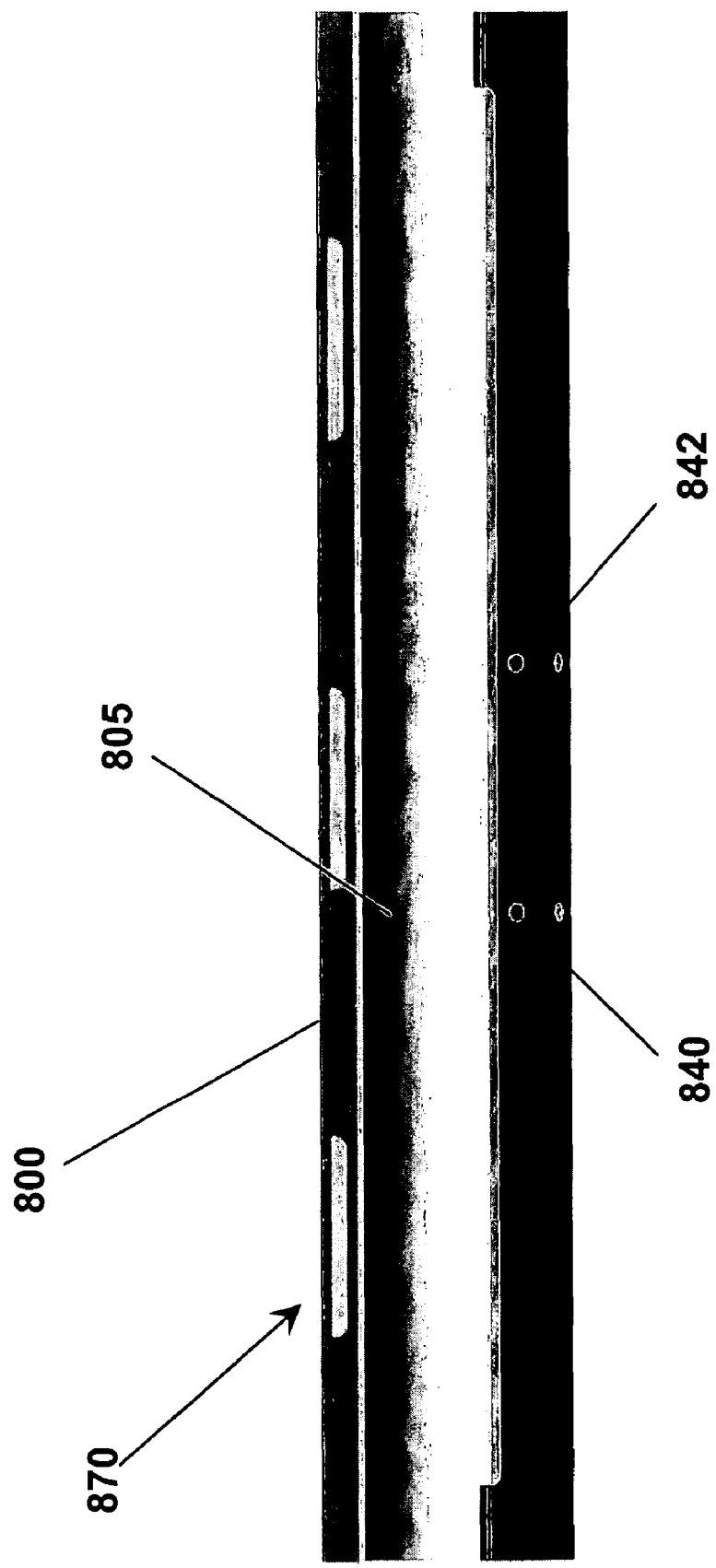
FIG. 23 is a cross sectional view of coupled tube and insulating material of the second embodiment.
Figure 24:
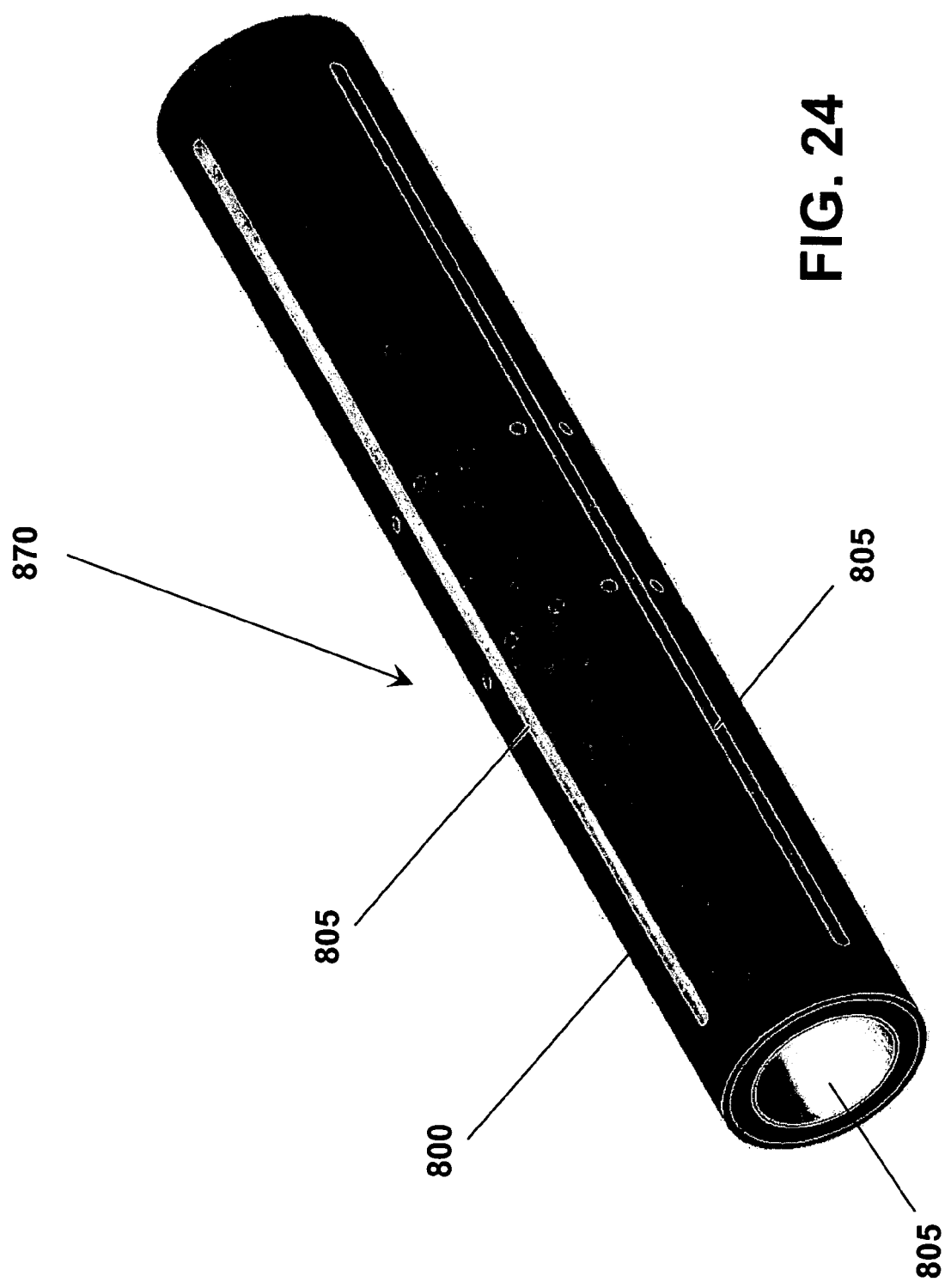
FIG. 24 is a perspective view of the coupled tube and insulating material of the second embodiment.
Figure 25:
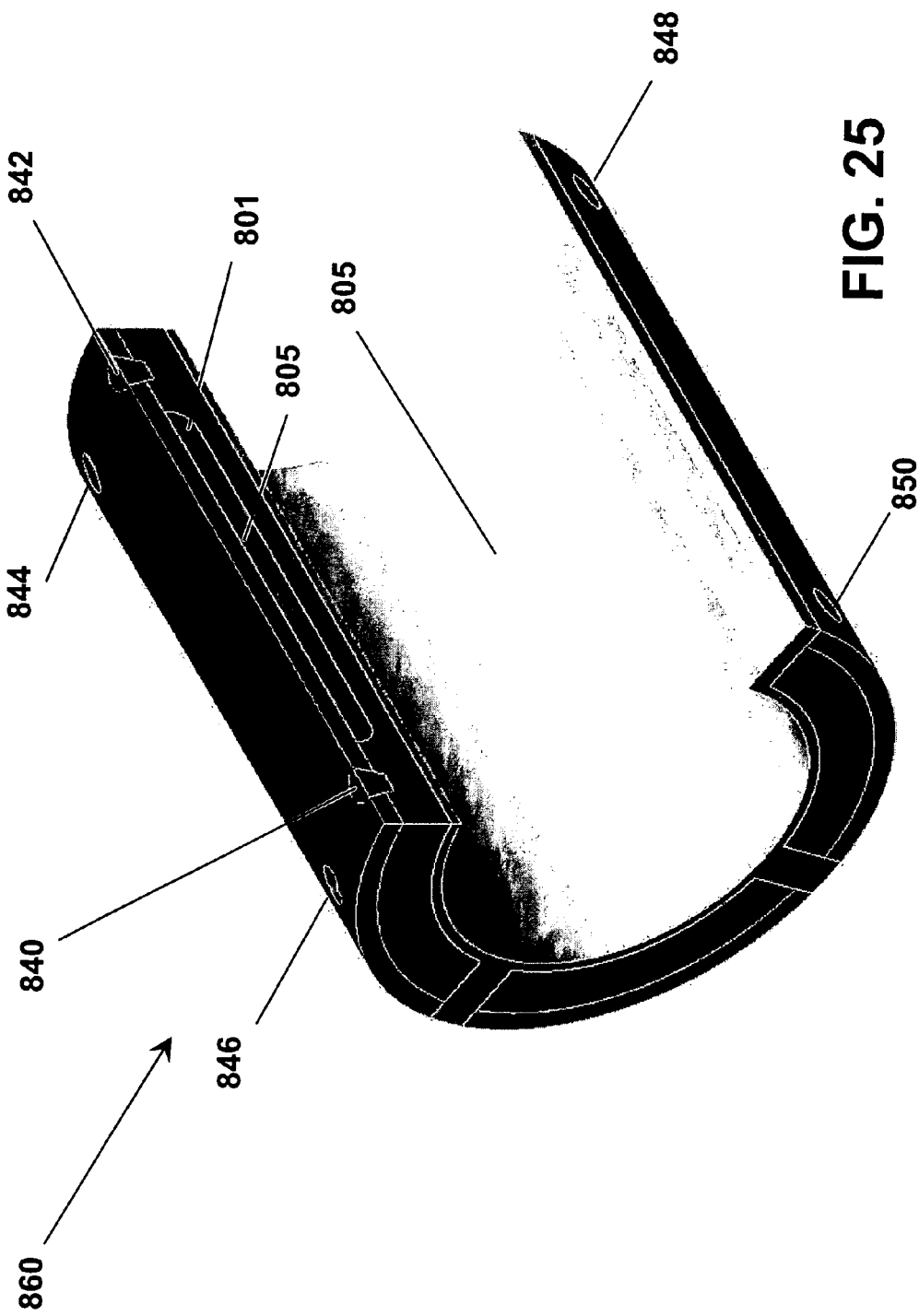
FIG. 25 is a perspective cut away view of a segmented electrode assembly cut from the second embodiment coupled tube and insulating material.
Figure 26:
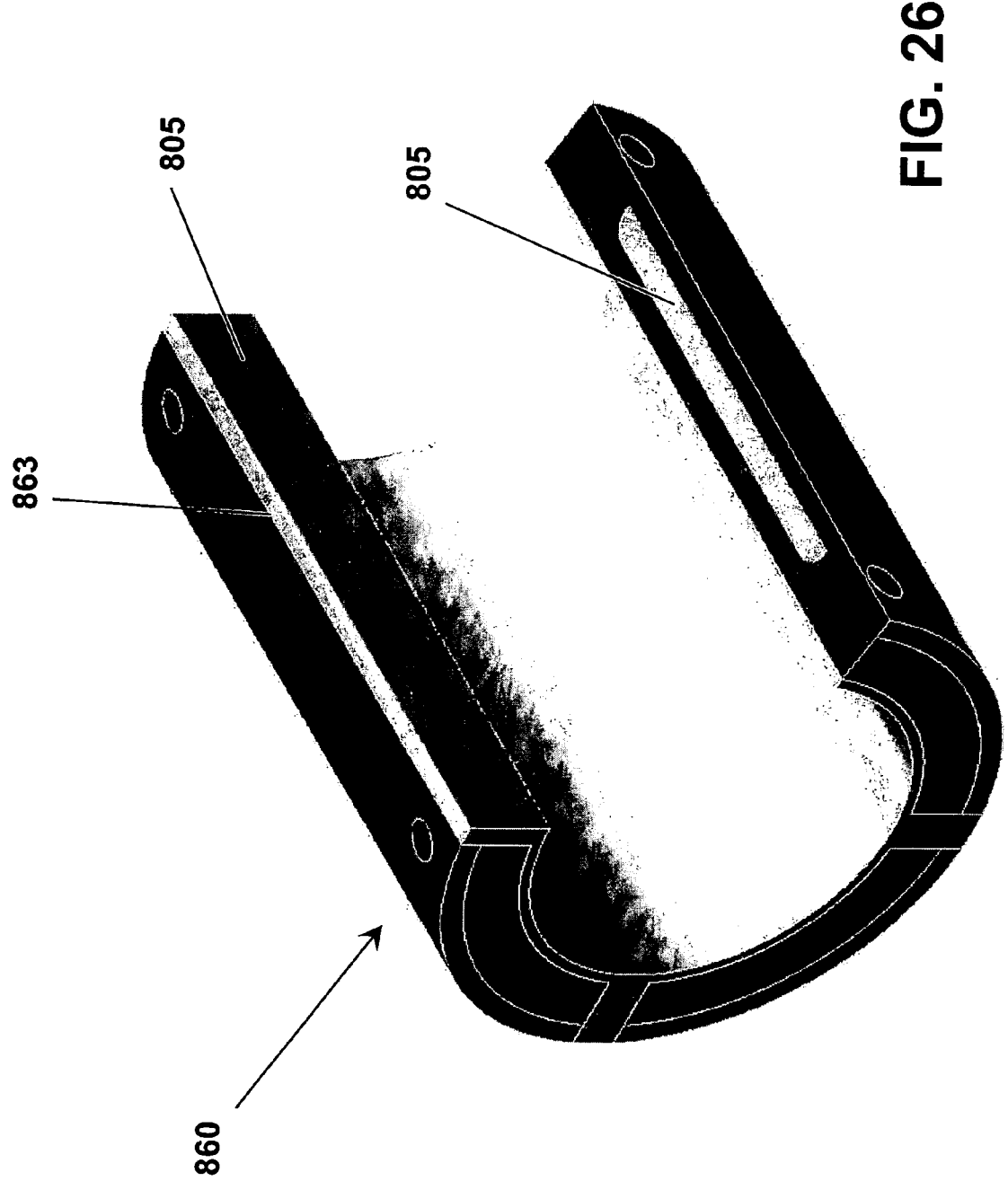
FIG. 26 is a different cut away view of the device of FIG. 25.
Figure 27:
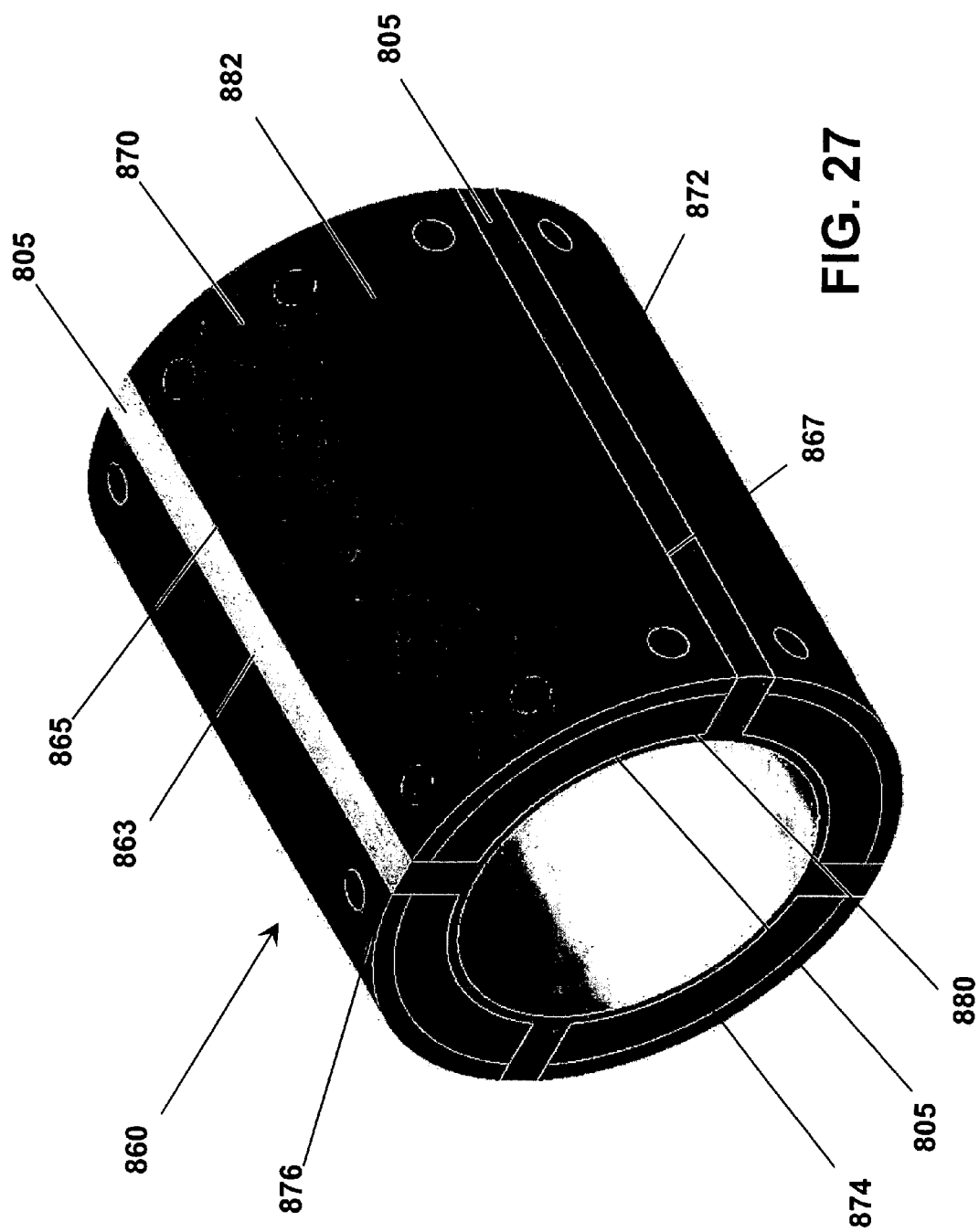
FIG. 27 is a perspective view of the device of FIGS. 25 and 26.
Figure 28:
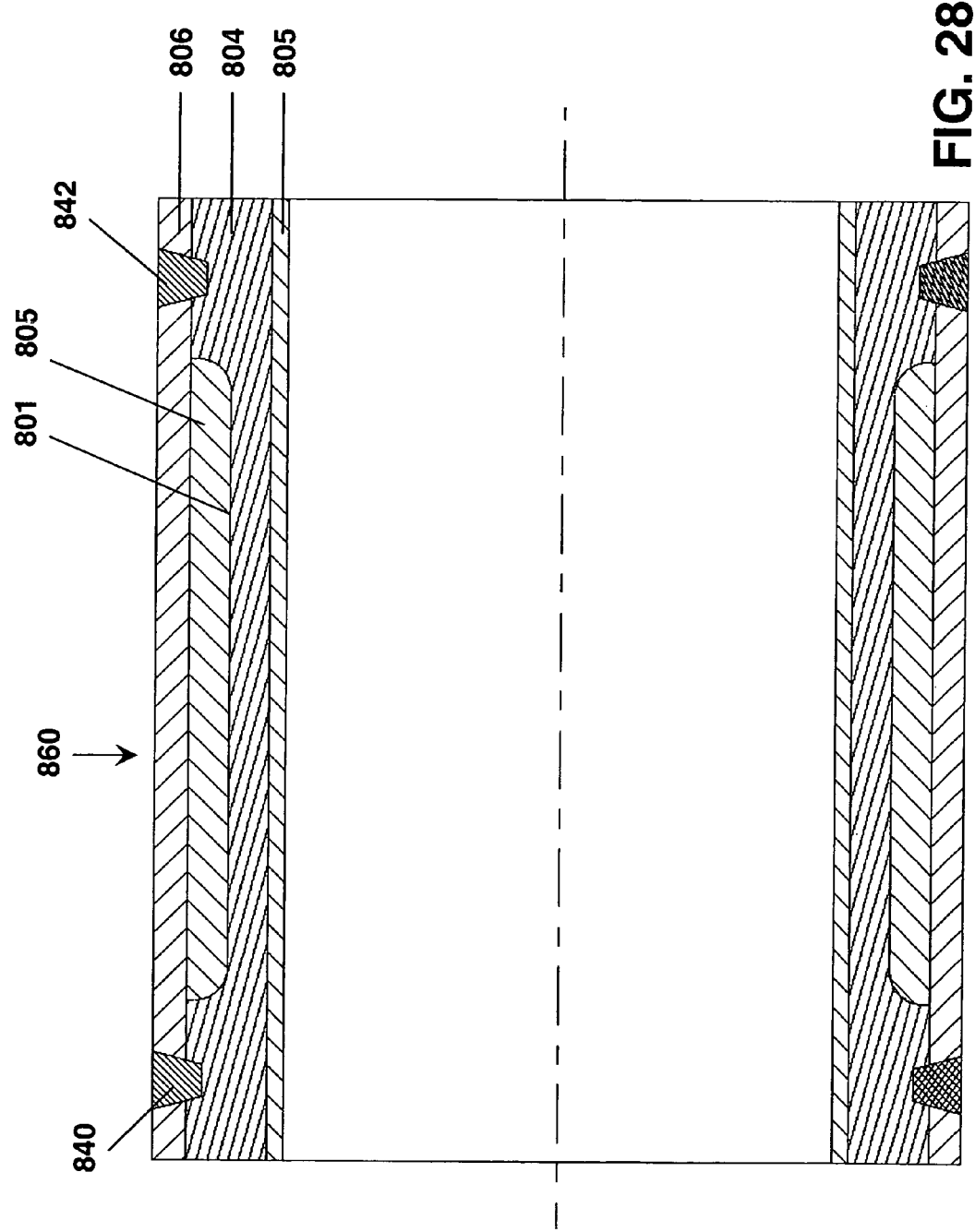
FIG. 28 is a cross sectional view of the device of FIGS. 25-27.

In one embodiment of an inner component, the outer surface of the inner component includes one or more higher portions and one or more lower portions. A higher portion has a greater diameter than a lower portion. Inner component 804 includes four higher portions 824, 826, 828, 830 and three lower portions 832, 834, and 836. The number of higher and lower portions may depend on how many segmented electrode assemblies are to be manufactured out of one tube. The particular embodiment shown in FIG. 19 is designed for manufacturing three segmented electrode assemblies from one tube by making four transverse cuts (perpendicular to the longitudinal axis of the tube) at the four higher portions.

At block 404 the inner component and outer component are aligned so that at least one of the gaps of the inner component is aligned with at least one of the gaps of the outer component. In the embodiment shown in FIGS. 18-28, all four gaps of the inner component 804 are aligned with all four gaps of the outer component 806. This will result in the segmented electrode assemblies having 4 electrically isolated segments.

At block 406, the inner component is attached to the outer component resulting in a tube. For example, inner component 804 is attached to outer component 806 by welding, resulting in tube 800. See for example weld locations 840, 842, 844, 846, 848 and 850. For purposes of this application, welding includes brazing.

The higher and lower portions of the inner component result in a passageway between the outer component and the inner component for each lower portion. A passageway for purposes herein is defined as an encapsulated space wherein the only inlets or outlets to the encapsulated space are through one or more gaps, using the definition of the term "gap" above. See for example, passageways 801, 803, and 807 in FIG. 20. The passageways fill or partially fill with the injected electrically insulating material as shown in FIGS. 21-24 that show one embodiment of a coupled tube and electrically insulating material 870. Electrically insulating material 805 extends into the passageways 801, 803 and 807. The existence of the electrically insulating material in the passageway or passageways provides additional retention of the segments. FIGS. 25-28 show various views of a segmented electrode assembly 860 after being cut from the coupled tube and electrically insulating material 870. The embodiment segmented electrode assembly shown in FIG. 27 includes four segments (870, 872, 874 and 876) each separated by a gap from the adjacent segments. The electrically insulating material 805 extends circumferentially along the inner surface 880 of the segment, in the gaps, and into the four passageways (not visible in FIG. 27).

The steps of FIGS. 3 and 4 are one embodiment method for making the segmented electrode assemblies of the second, third and fourth embodiments. Note also that once the inner component is attached to the outer component and the bridges removed or partially removed to form a segmented electrode assembly (such as assembly 860 in FIGS. 25-28, the segments (e.g., 870, 872, 874 and 876) have an inner surface (e.g., inner surface 880 of segment 870) and an outer surface (e.g., outer surface 882 of segment 870). The inner surface of a segment is the surface facing inward toward the eventual conductor assembly and the outer surface is the surface of the segment that face the human tissue upon implantation. A segment may also have longitudinal edge surfaces. A longitudinal edge surface is a surface of a segment adjacent a gap. See for example, longitudinal edge surfaces 863, 865 and 867 in FIGS. 26 and 27. Longitudinal edge surfaces 865 and 867 are a part of segment 870. Longitudinal edge surface 863 is part of segment 876. Insulating material 805 extends between longitudinal edge surfaces 865 and 867.

Furthermore, a segmented electrode assembly of the second, third and fourth embodiments may be used to make a medical lead by the same process as described above with respect to FIGS. 7 and 12-17.

Figure 38:
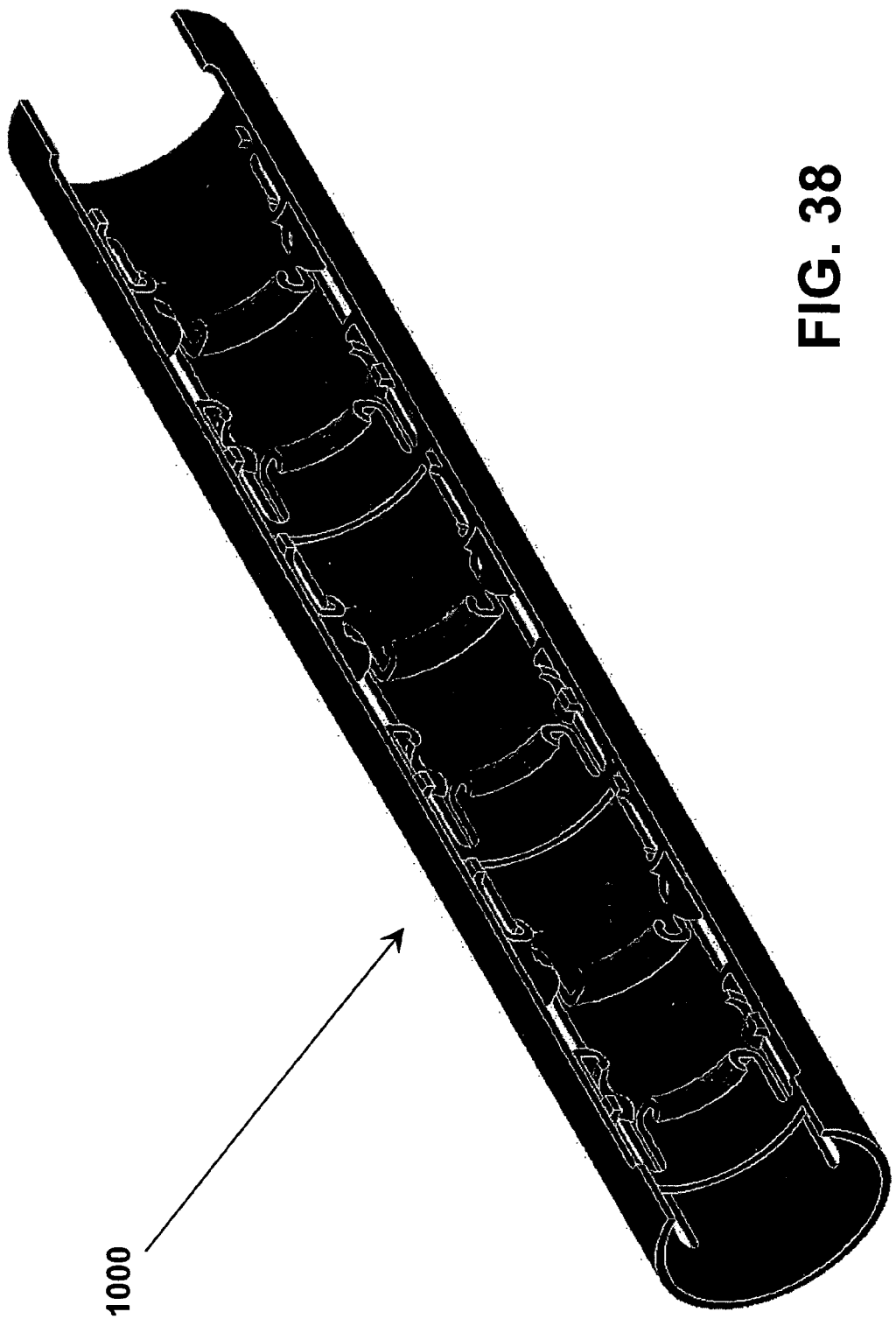
FIG. 38 is a different perspective cut away view of the tube of FIG. 36.
Figure 39:
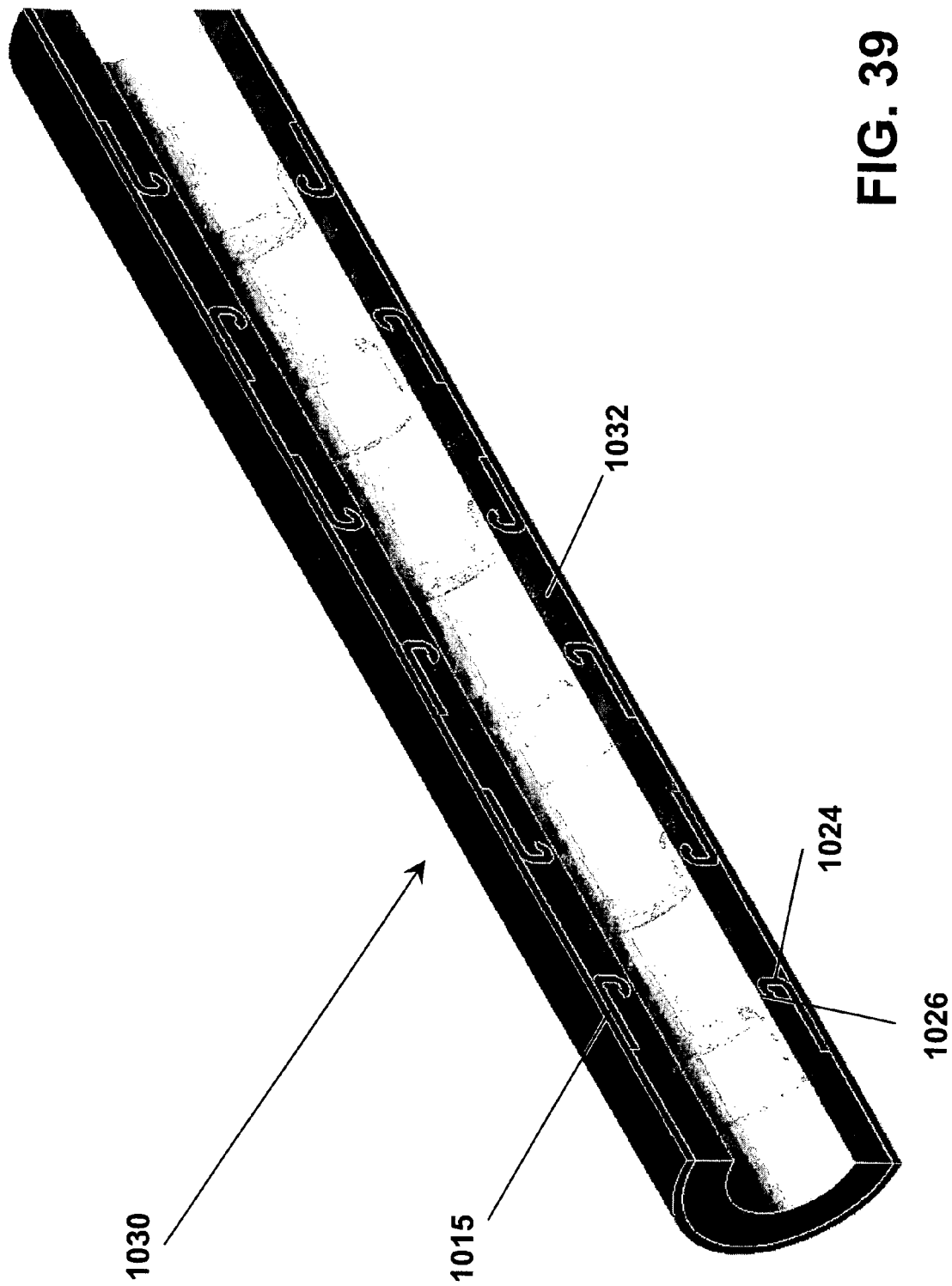
FIG. 39 is a perspective cut away view of the tube of FIG. 36 after being coupled with electrically insulating material.
Figure 40:
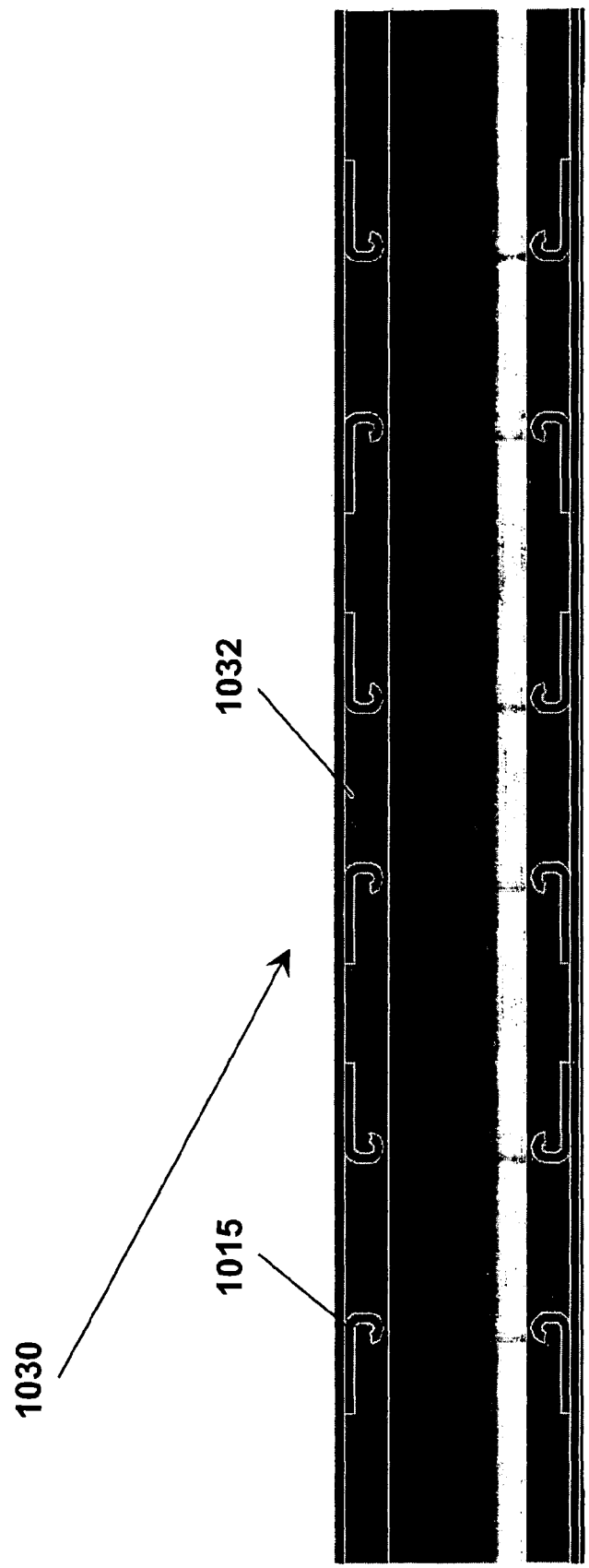
FIG. 40 is a cross sectional view of the coupled tube and electrically insulating material of FIG. 39.
Figure 41:
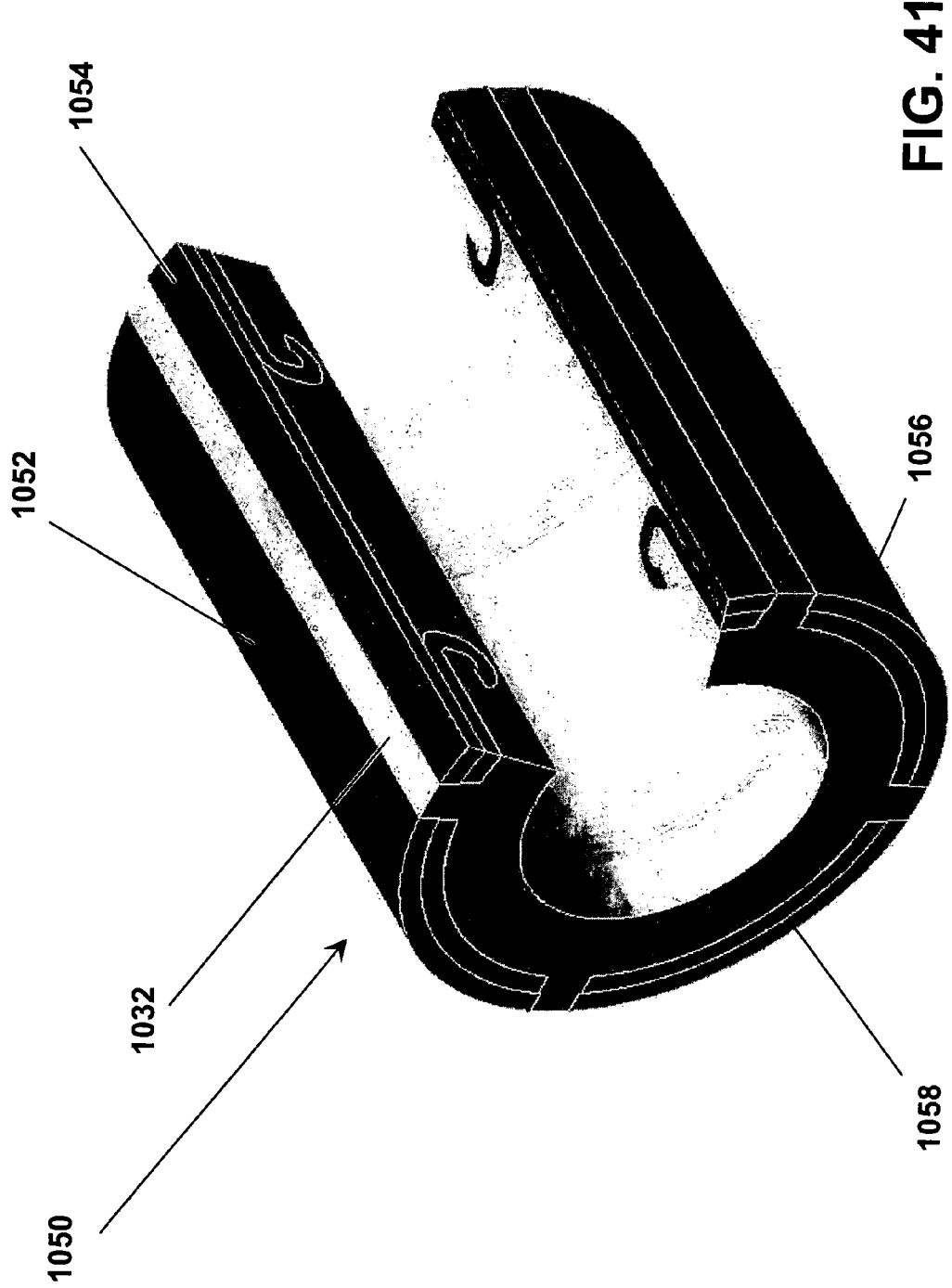
FIG. 41 is a perspective cut away view of a segmented electrode assembly cut from the coupled tube and electrically insulating material of FIG. 40.
Figure 42:
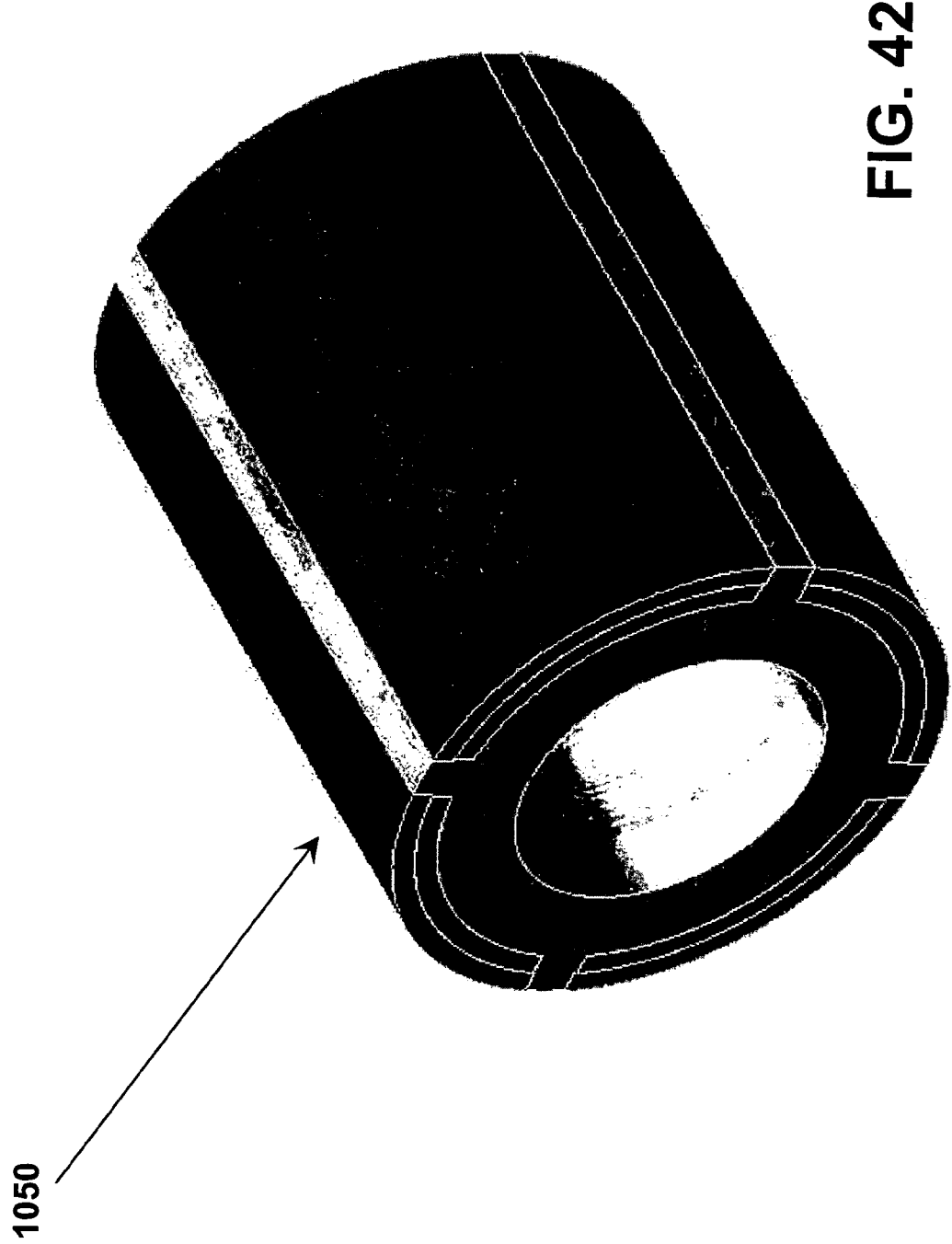
FIG. 42 is another view of the embodiment of FIG. 41.
Figure 43:
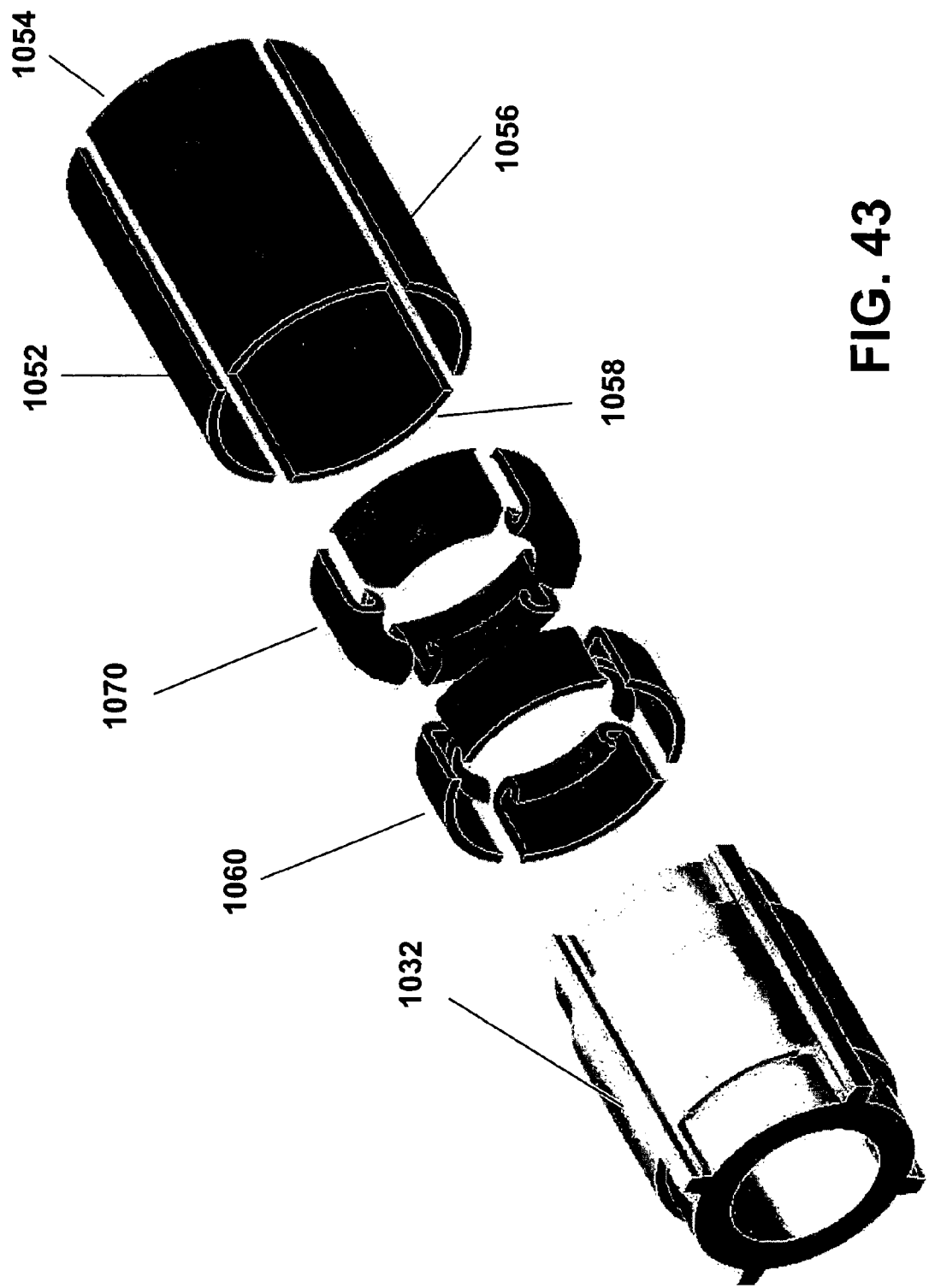
FIG. 43 is an exploded perspective view of the components in the embodiment segmented electrode assembly of FIGS. 41 and 42.

FIGS. 36-43 show another embodiment tube and resulting segmented electrode assembly according to the steps of FIG. 5. In this embodiment there may be one or more inner components 1002, 1004, 1006, 1008, 1010 and 1012, and an outer component 1014 that make up the tube 1000. Outer component includes four gaps such as ga 1016. Inner components include one or more gaps such as gaps 1018 and 1020. The inner components include a protrusion extending inward toward the inside of the inner component and configured to anchor the segments in the electrically insulating material. The protrusion may include a first portion that is generally perpendicular to the inner surface of the inner component and a second portion that is generally perpendicular to the first portion. This second portion is an undercut surface and it provides the anchoring of the segment in the electrically insulating material. In the embodiment shown in FIGS. 36-43, the protrusion is a hook shaped protrusion such as hook 1015. The first portion that is generally perpendicular to the inner surface 1022 is identified as portion 1024, and the second portion that is generally perpendicular to the first portion 1024 is identified as second portion 1026 (see FIG. 37). Note that the first portion and second portion may be curved as long as they have at least a component of their direction be in the described directions. For example, second portion 1026 is curved but has a component of its position in a direction perpendicular to the first portion 1024. There may be at least one protrusion between each set of two adjacent gaps so that each segment is coupled to at least one protrusion for purposes of retaining the segment onto the lead. Note that in this embodiment, the inner components may include one or more bridges that are removed or partially removed after the electrically insulating material is coupled to the tube. One embodiment method of partially or wholly removing the bridges is by cutting through the coupled tube and electrically insulating material in a direction generally perpendicular to the longitudinal axis of the tube. Example cut locations are shown as 1003, 1005, 1007, 1009, 1011 and 1013 in FIG. 36. These cuts would result in three segmented electrode assemblies. Specifically the three assemblies would be those portions between cuts 1003 and 1005, between 1007 and 1009, and between 1011 and 1013. FIG. 38 is another view of the tube 1000 before being coupled with an electrically insulating material. FIGS. 39 and 40 show various views of a coupled tube and electrically insulating material 1030 according to this embodiment before partial or whole removal of the bridges. Electrically insulating material 1032 surrounds the hooks such as hook 1015. FIGS. 41 and 42 show different views of a segmented electrode assembly 1050 after being cut out of the coupled tube and electrically insulating material 1030. Assembly 1050 includes segments 1052, 1054, 1056 and 1058. These segments are now electrically insulated from each other by electrically insulating material 1032. FIG. 43 is an exploded view of the assembly 1050. 1060 and 1070 are the portions of segments 1052, 1054, 1056 and 1058 that originally came from the inner component of the tube.

Figure 29:
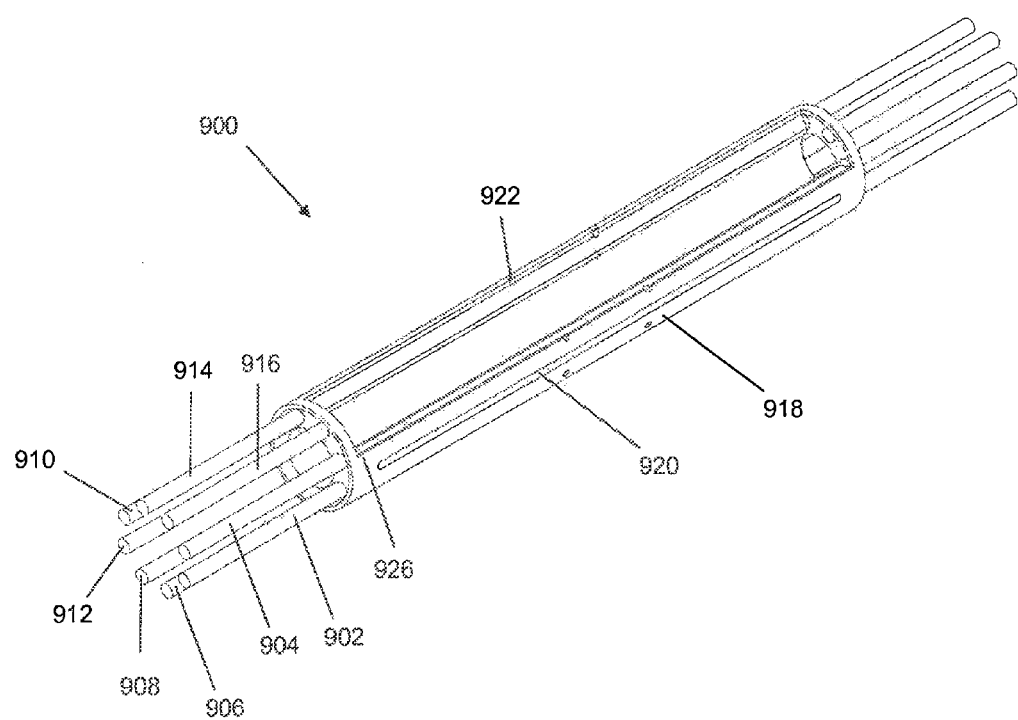
FIG. 29 is a perspective cut away view of a third embodiment coupled tube and insulating material.
Figure 30:
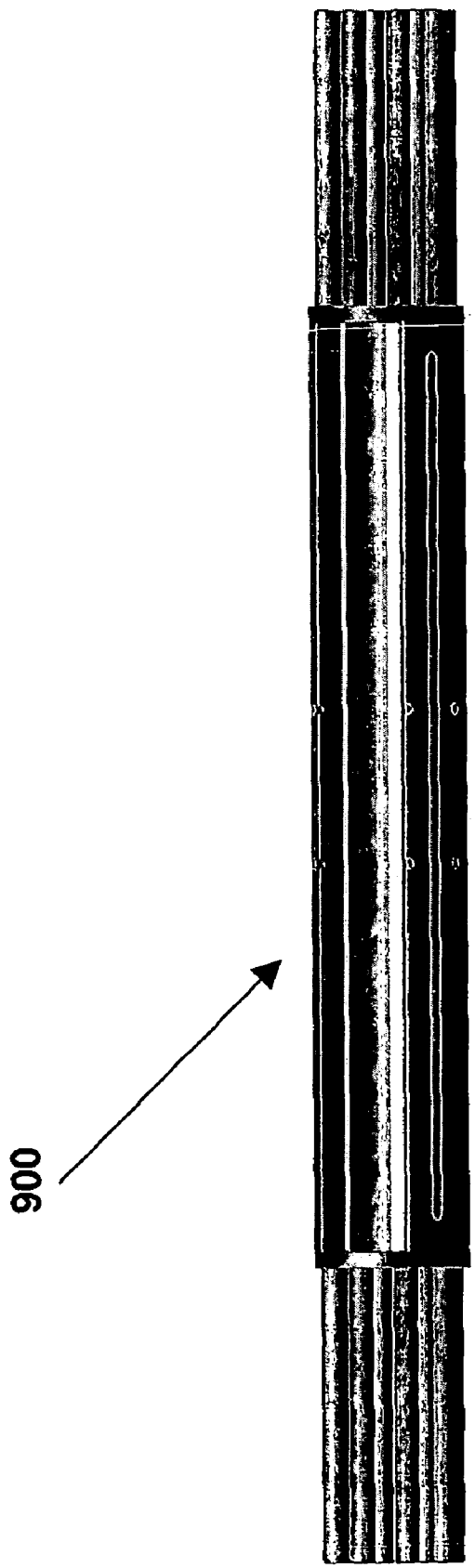
FIG. 30 is a cross sectional view of the embodiment of FIG. 29.
Figure 31:
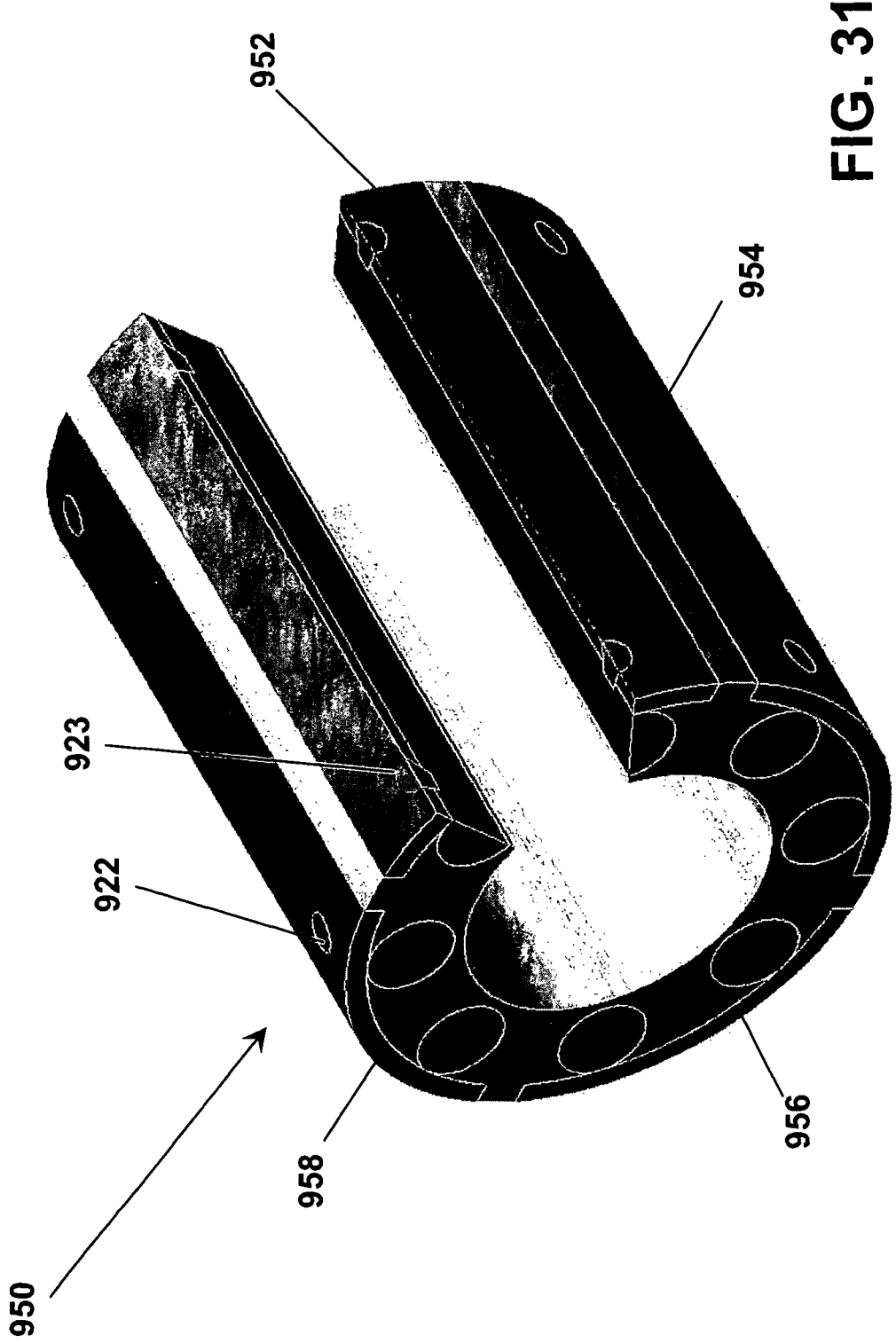
FIG. 31 is a perspective cut away view of a segmented electrode assembly cut from the embodiment of FIGS. 29-30.
Figure 32:
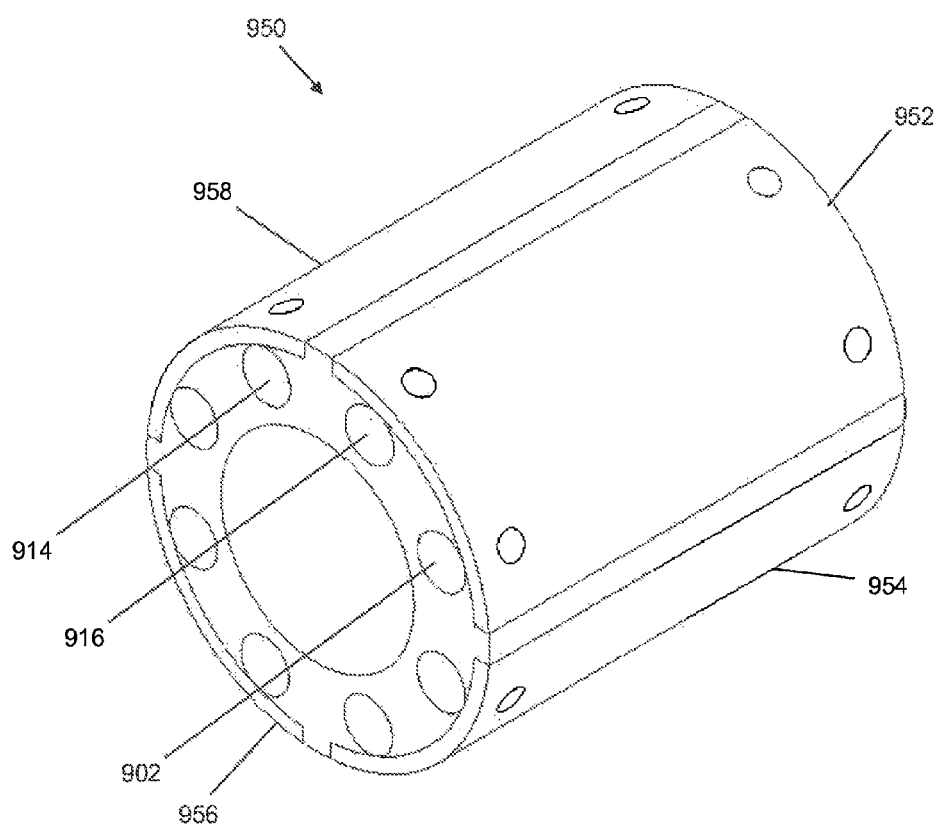
FIG. 32 is a perspective view of the segmented electrode assembly of FIG. 31.
Figure 33:
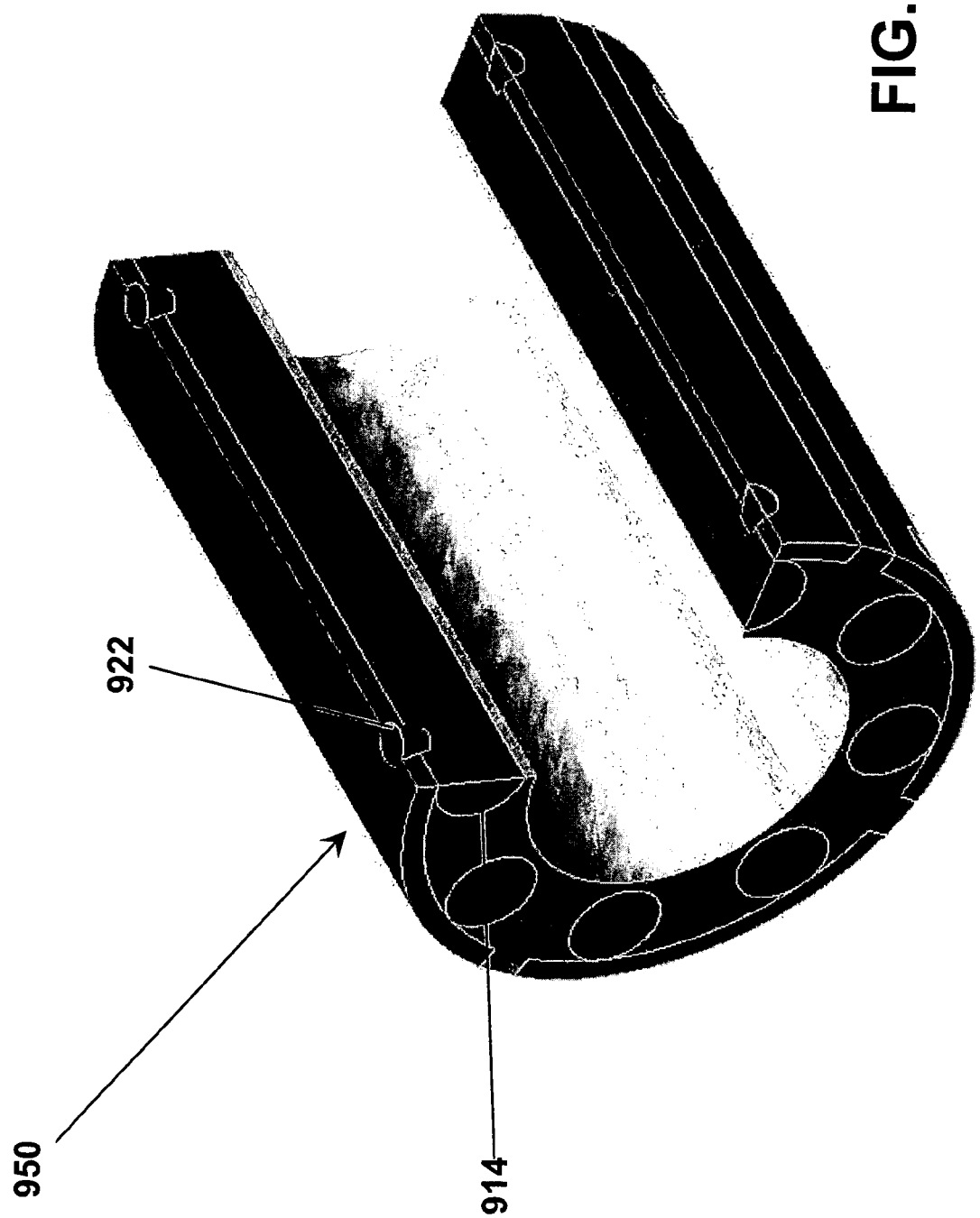
FIG. 33 is a different perspective cut away view of the segmented electrode assembly of FIG. 31.
Figure 34:
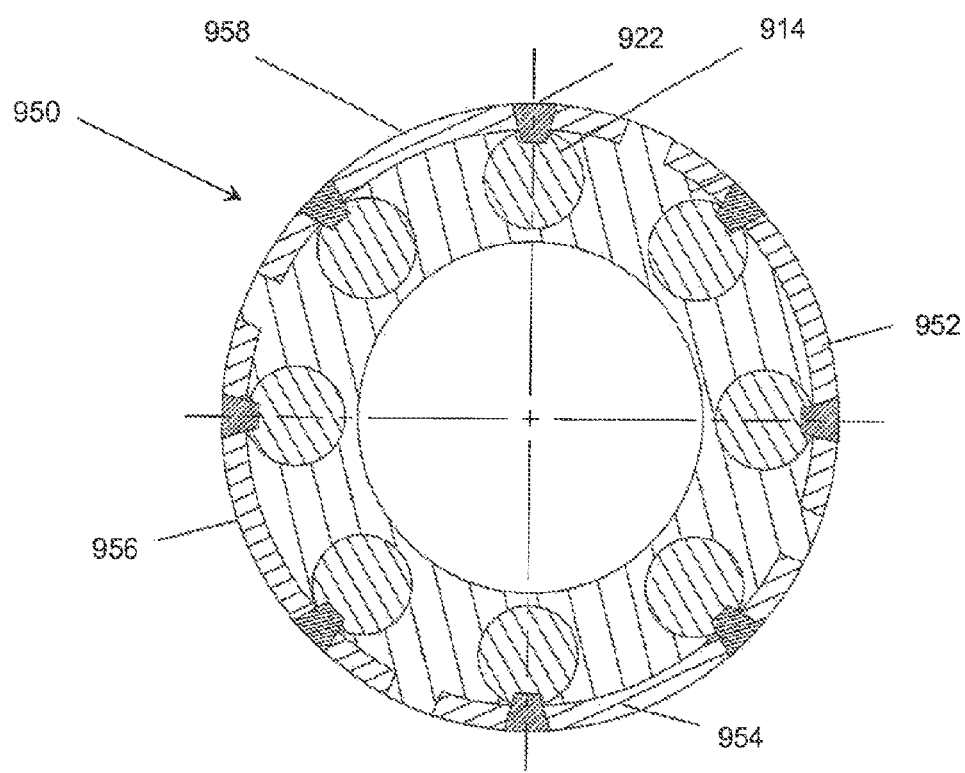
FIG. 34 is a cross sectional end view of the segmented electrode assembly of FIGS. 31-33.
Figure 35:
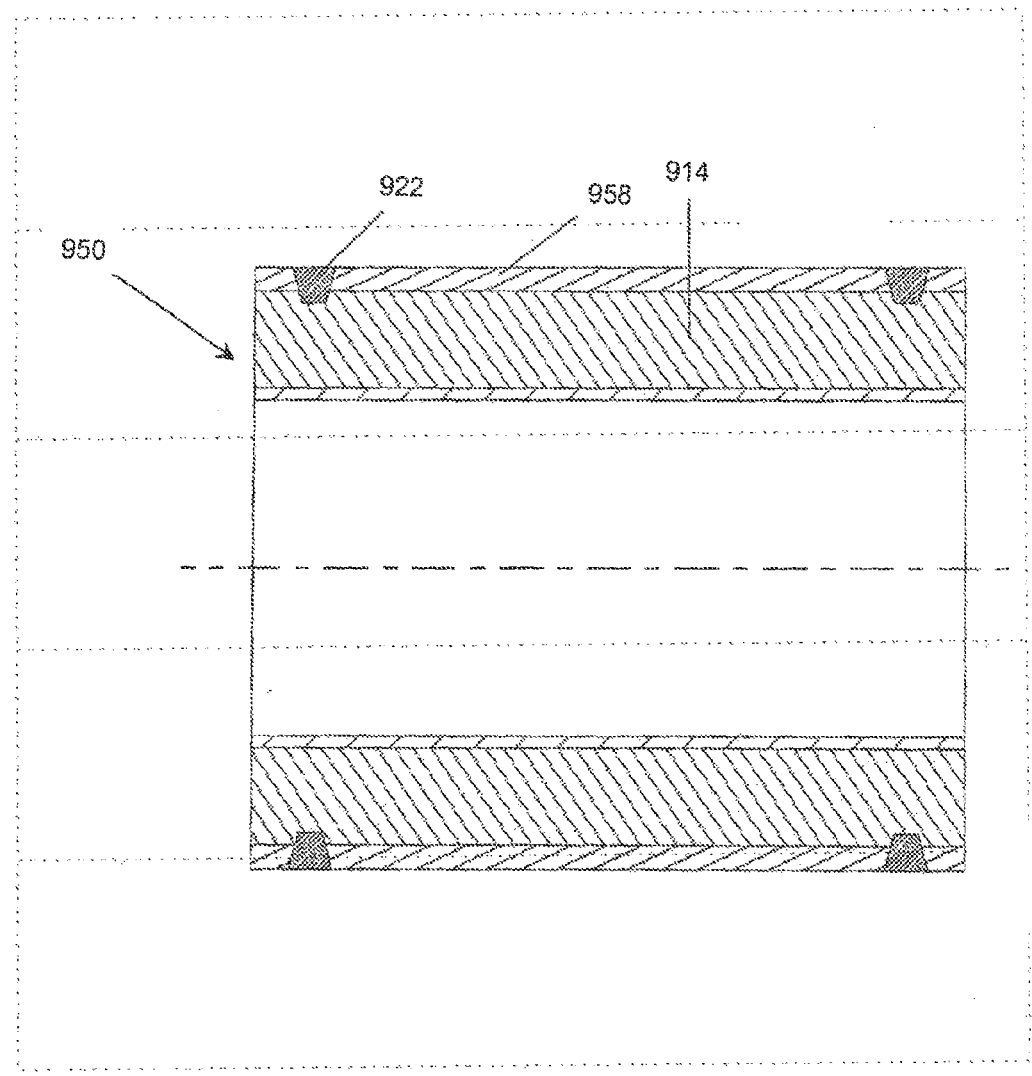
FIG. 35 is a cross sectional view perpendicular to the view of FIG. 34.
Figure 36:
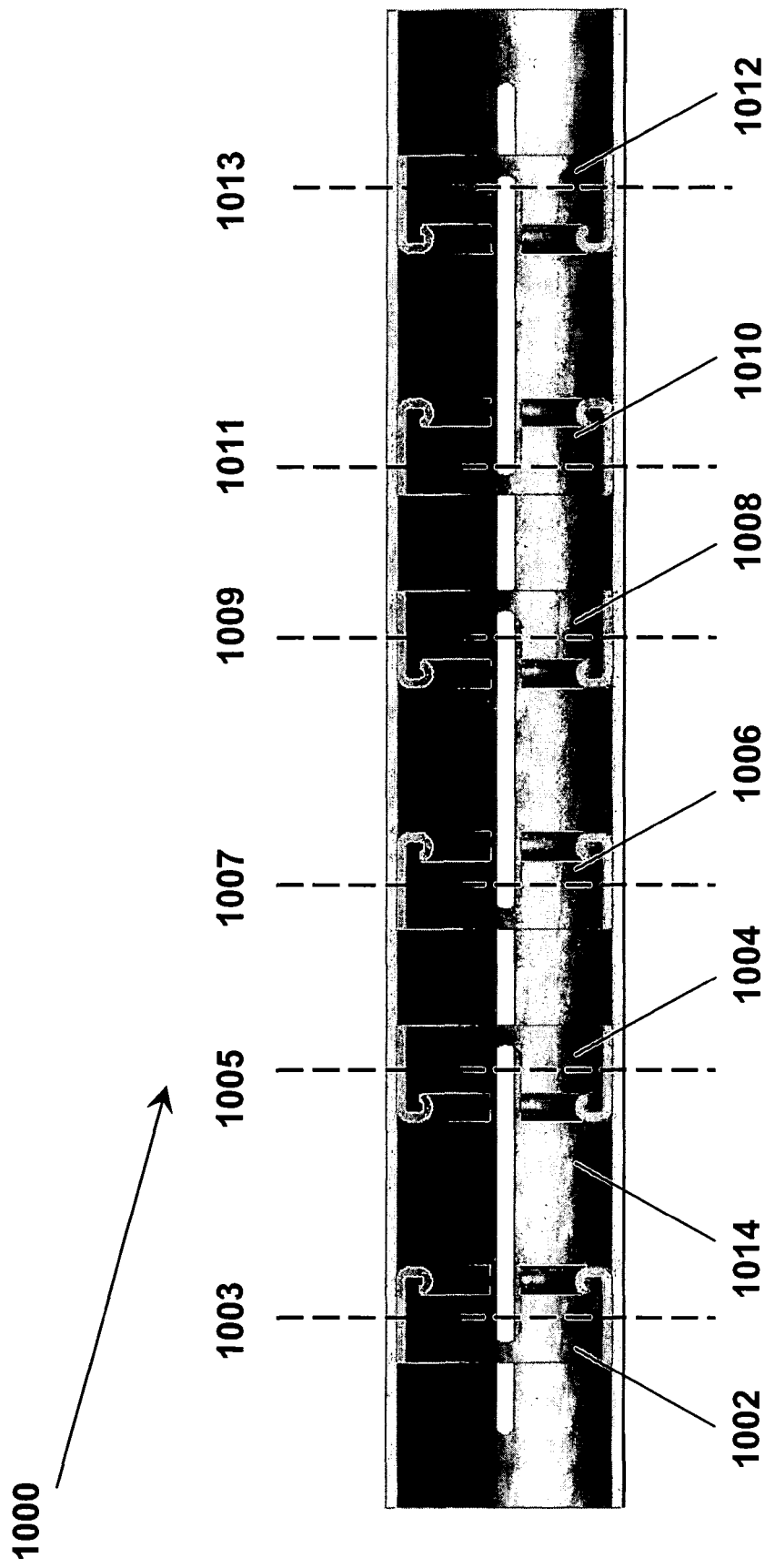
FIG. 36 is a cut away view of a fourth embodiment tube.
Figure 37:
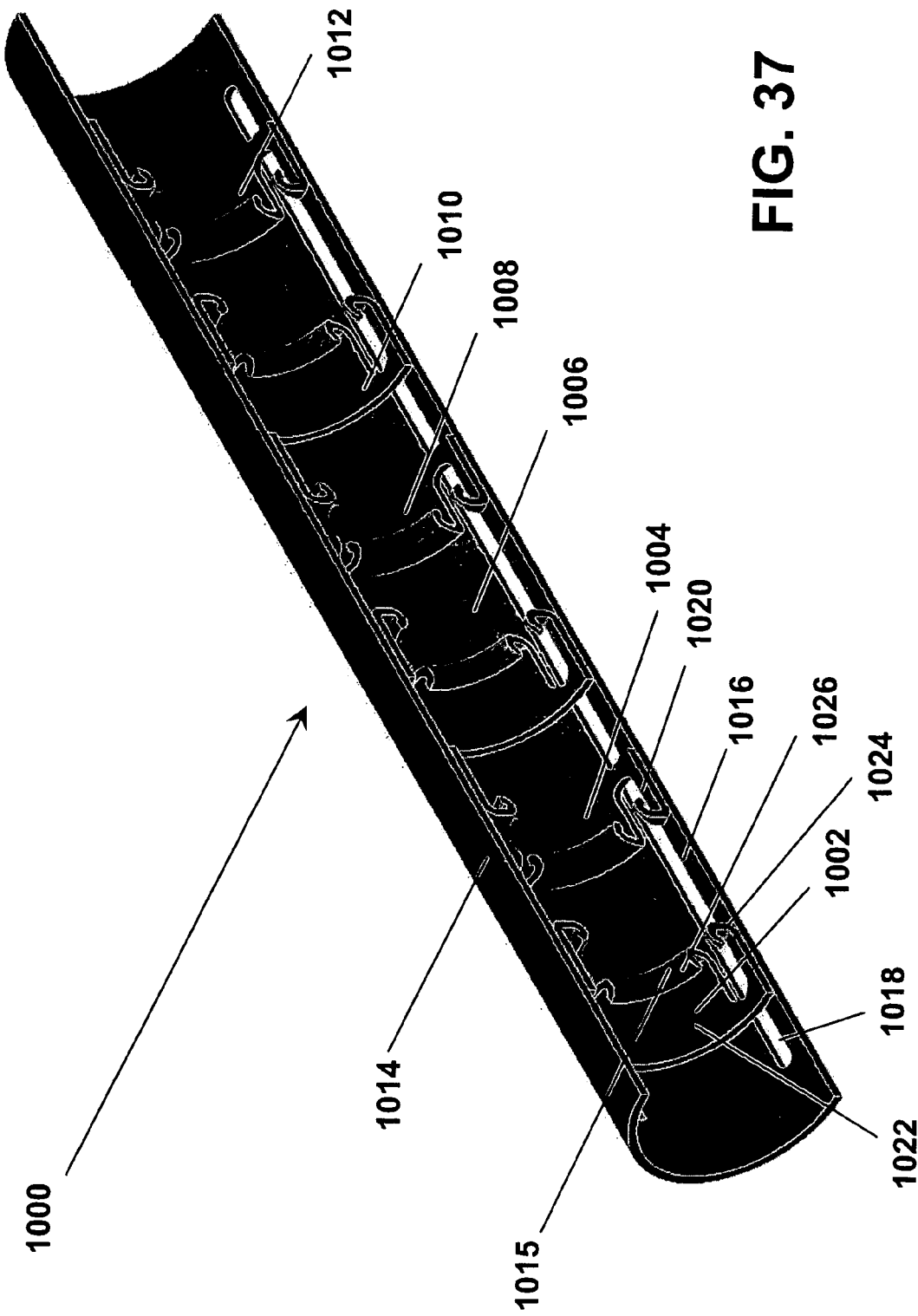
FIG. 37 is a perspective cut away view of the tube of FIG. 36.

FIG. 6 is a flowchart showing an alternative step to making a tube. FIGS. 29-35 show an alternative embodiment tube and resulting segmented electrode assemblies made according to the flowchart of FIG. 6. At block 502, one or more rods are attached to an inner surface of an outer component. There may be one rod per segment or multiple rods per segment. In the embodiment of FIGS. 29-35, there are two rods per segment. The outer component is defined the same as discussed above with earlier embodiments. "Rod" means any member extending substantially along the full length or greater of the outer component when situated parallel to the longitudinal axis of the outer component. Rods may be of any shape such that once attached to a segment and coupled with electrically insulating material, there is electrically insulating material between any point on the rod and any point on the segment along a line passing through such point on the segment and perpendicular to a tangent to the segment. In the embodiment shown in FIG. 29-35, there are eight rods (902, 904, 906, 908, 910, 912, 914, 916) and they are cylindrical and hollow in shape. The rods are attached to the outer component. In the embodiment of FIGS. 29-35, the rods are attached to the outer component 918 by welding. See for example, weld locations 922 and 923. Note also that outer component 918 has gaps such as gap 920, and bridges such as bridge 926. In FIGS. 29 and 30, the rods have been welded to the outer component and to form a tube. The tube has been coupled to polyurethane by placing the tube into a mold and injecting the polyurethane into the mold. The resulting coupled tube and electrically insulating material 900 is shown.

FIGS. 31-35 show various views of a segmented electrode assembly 950 that has been cut from the coupled tube and insulating material 900. The assembly 950 includes segments 952, 954, 956 and 958.

The various segmented electrodes may be activated to deliver electric pulses or deactivated independently of each other. In alternative embodiments in which it may be desired to reduce the number of conductors in the lead, segments may be electrically coupled together. For example, in a DBS application with 4 quarter segments, the two opposite segments could be electrically coupled together. Electrically coupling segments together may be accomplished by welding the same conductor to both segments or by leaving a bridge between the two segments.

Thus, embodiments of the method of manufacturing a medical lead are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of manufacturing a segmented electrode assembly comprising:
   coupling an electrically conductive tube to an electrically insulating material, wherein the tube is generally cylindrical and has an imaginary longitudinal axis, wherein the tube defines one or more gaps at a first axial position, and wherein the tube comprises at least a first bridge located at a second axial position;
   removing at least a portion of the first bridge resulting in a segmented electrode assembly having at least one segment.

2. The method of claim 1 wherein removing at least a portion of the first bridge comprises cutting through the tube in a direction generally perpendicular to the longitudinal axis at a cutting location between the first and second axial positions of the tube resulting in the first bridge being disconnected from the tube.

3. The method of claim 1 wherein the tube further comprises a second bridge at a third axial position and wherein the second axial position is at a first end of the tube and the third axial position is at a second end of the tube, and wherein the method further comprises removing at least a portion of the second bridge.

4. The method of claim 3 wherein removing at least a portion of the first bridge comprises cutting off the first end of the tube resulting in removal of the first bridge from the tube and wherein removing at least a portion of the second bridge comprises cutting off the second end of the tube resulting in removal of the second bridge from the tube.

5. The method of claim 1 wherein the one or more gaps comprise a first gap at a first circumferential location of the first axial position and a second gap at a second circumferential location of the first axial position, and wherein the first bridge is adjacent to the first gap, and wherein the tube has a second bridge adjacent to the second gap, the method further comprising removing at least a portion of the second bridge resulting in a segmented electrode assembly.

6. The method of claim 1 wherein coupling the tube with an electrically insulating material comprises placing the tube into a mold and injecting the electrically insulating material into the mold.

7. The method of claim 6 further comprising drilling a hole through the electrically insulating material in an axial direction to provide space capable of receiving electrical conductors.

8. The method of claim 7 further comprising placing a conductor assembly comprising one or more electrical conductors through the hole and electrically coupling at least one of the one or more conductors to the segment.

9. The method of claim 8 wherein the one or more electrical conductors of the conductor assembly are coiled.

10. The method of claim 9 wherein the conductor assembly includes a stylet receiving member and the electrical conductors of the conductor assembly are coiled around the stylet receiving member.

11. The method of claim 10 wherein the stylet receiving member defines a lumen that is configured for receipt of a stylet wire.

12. The method of claim 6 wherein coupling the tube with an electrically insulating material further comprises retaining a pin along the axis of the tube in the mold for preserving space along the longitudinal axis of the tube capable of receiving electrical conductors.

13. The method of claim 6 further comprising machining at least one end slot in the segmented electrode assembly configured for electrical connection of an electrical conductor to the segment.

14. The method of claim 1 further comprising placing a conductor assembly comprising one or more electrical conductors along the longitudinal axis of the segmented electrode assembly and electrically coupling at least one of the one or more conductors to the segment.

15. The method of claim 1 further comprising making the tube wherein making the tube comprises:
   placing an inner component into an outer component; wherein the inner component is generally cylindrical and hollow, and wherein the inner component defines one or more gaps at the first axial position, and wherein the inner component comprises at least a second bridge located at the second axial position, and wherein the inner component further comprises an inner surface and an outer surface, and wherein the outer surface comprises a first higher portion having a first diameter and a first lower portion having a second diameter, wherein the first diameter is greater than the second diameter; and wherein the outer component comprises an electrically conducting material, wherein the outer component is generally cylindrical and hollow, and wherein the outer component defines one or more gaps at the first axial position, and wherein the outer component comprises at least a third bridge located at the second axial position, and wherein the outer component further comprises an inner surface and an outer surface wherein the inner surface has a third diameter larger than the first diameter;
   aligning at least one of the one or more gaps of the inner component with at least one of the one or more gaps of the outer component;
   attaching the inner component to the outer component wherein the first bridge comprises the second and third bridges, and wherein at least one passageway is created between the inner component and the outer component adjacent to the lower portion.

16. The method of claim 15 wherein the inner component is an electrically conducting material, and wherein attaching the inner component to the outer component comprises welding the inner component to the outer component.

17. The method of claim 15 wherein coupling the tube with an electrically insulating material comprises placing the tube into a mold and injecting the electrically insulating material into the mold, and wherein the electrically insulating material is injected into the at least one passageway.

18. The method of claim 15 wherein the inner component further comprises a second and third higher portions, and a second lower portion, wherein the order of the higher and lower portions along the longitudinal axis is first higher portion, first lower portion, second higher portion, second lower portion, and then third higher portion, and wherein the method further comprises cutting the coupled tube and electrically insulating material at least at the second higher portion and at the third higher portion, resulting in at least two segmented electrode assemblies.

19. The method of claim 1 further comprising making the tube wherein making the tube comprises:
attaching one or more rods to an inner surface of an outer component, wherein the outer component comprises an electrically conducting material, wherein the outer component is generally cylindrical and hollow, and wherein the outer component defines one or more gaps at the first axial position, and wherein the first bridge in the tube comprises a bridge in the outer component located at the second axial position.

20. The method of claim 19 wherein attaching the one or more rods to the inner surface of the outer component comprises welding the one or more rods to the inner surface of the outer component.

21. The method of claim 19 wherein attaching one or more rods to the inner surface of the outer component comprises attaching two rods to each segment.

22. The method of claim 19 wherein a rod comprises a cylindrical shaped member.

23. The method of claim 19 wherein the rod is hollow.

24. The method of claim 1 further comprising making the tube wherein making the tube comprises:
placing an inner component into an outer component; wherein the inner component is generally cylindrical and hollow and therefore defining a hollow space, and wherein the inner component defines one or more gaps at the first axial position, and wherein the inner component comprises at least a second bridge located at the second axial position, and wherein the inner component further comprises a protrusion extending into the hollow space, wherein the protrusion is configured to anchor the segments in the electrically insulating material; and wherein the outer component comprises an electrically conducting material, wherein the outer component is generally cylindrical and hollow, and wherein the outer component defines one or more gaps at the first axial position, and wherein the outer component comprises at least a third bridge located at the second axial position;
aligning at least one of the one or more gaps of the inner component with at least one of the one or more gaps of the outer component;
attaching the inner component to the outer component wherein the first bridge comprises the second and third bridges.

25. The method of claim 24 wherein the protrusion comprises a first portion generally perpendicular to the inner surface of the inner component and a second portion that is distal to the first portion, wherein at least part of the second portion is generally perpendicular to the first portion.

26. The method of claim 25 wherein the protrusion is generally shaped like a hook.

27. The method of claim 24 wherein attaching the inner component to the outer component comprises welding the inner component to the outer component.

28. The method of claim 1 wherein the tube comprises an alloy of platinum and iridium and the electrically insulating material comprises polysulfone or PEEK.

29. A method of manufacturing a medical lead comprising:
performing the steps of claim 1 to make a first segmented electrode assembly;
placing the first segmented electrode assembly on a conductor assembly comprising at least a first electrical conductor, wherein the conductor assembly is positioned along the longitudinal axis of the first segmented electrode assembly;
electrically coupling the first conductor to a first segment of the first segmented electrode assembly;
placing the coupled conductor assembly and first segmented electrode assembly into a mold;
injecting an electrically insulating material into the mold to create a medical lead having a substantially cylindrical shape.

30. The method of claim 29 wherein placing the first segmented electrode assembly on the conductor assembly comprises sliding the first segmented electrode assembly onto the conductor assembly in the direction along the longitudinal axis.

31. The method of claim 29 wherein the first segmented electrode assembly has a cross sectional arc less than 360 degrees such that there is an opening in the arc of the first segmented electrode assembly, and wherein placing the first segmented electrode assembly on the conductor assembly comprises moving the first segmented electrode assembly and the conductor assembly relative to each other and in a direction having a component that is perpendicular to the longitudinal axis of the first segmented electrode assembly such that the conductor assembly passes through the opening.

32. The method of claim 29 wherein injecting the electrically insulating material into the mold comprises injecting the electrically insulating material into the mold at a pressure less than 1000 psi.

* * * * *